(12) United States Patent
Kakeshita et al.

(10) Patent No.: US 11,542,499 B2
(45) Date of Patent: Jan. 3, 2023

(54) MODIFIED PROMOTER

(71) Applicant: Kao Corporation, Tokyo (JP)

(72) Inventors: Hiroshi Kakeshita, Wakayama (JP);
Nozomu Shibata, Wakayama (JP);
Yosuke Shida, Nagaoka (JP); Wataru Ogasawara, Nagaoka (JP)

(73) Assignee: Kao Corporation, Tokyo (JP)

( * ) Notice: Subject to any disclaimer, the term of this patent is extended or adjusted under 35 U.S.C. 154(b) by 576 days.

(21) Appl. No.: 16/635,311

(22) PCT Filed: Aug. 1, 2018

(86) PCT No.: PCT/JP2018/028937
§ 371 (c)(1),
(2) Date: Jan. 30, 2020

(87) PCT Pub. No.: WO2019/031368
PCT Pub. Date: Feb. 14, 2019

(65) Prior Publication Data
US 2021/0087553 A1 Mar. 25, 2021

(30) Foreign Application Priority Data

Aug. 9, 2017 (JP) ............................ JP2017-153983
Jul. 31, 2018 (JP) ............................ JP2018-143957

(51) Int. Cl.
*C12N 5/10* (2006.01)
*C12N 15/11* (2006.01)
*C12N 15/80* (2006.01)
*C12N 9/24* (2006.01)

(52) U.S. Cl.
CPC .............. *C12N 15/111* (2013.01); *C12N 5/10* (2013.01); *C12N 15/80* (2013.01); *C12Y 302/01008* (2013.01); *C12N 9/2402* (2013.01); *C12N 2830/00* (2013.01)

(58) Field of Classification Search
CPC .... C12N 15/111; C12N 2830/00; C12N 5/10; C12Y 302/01008
See application file for complete search history.

(56) References Cited

U.S. PATENT DOCUMENTS

| 2013/0196374 A1 | 8/2013 | Koishihara |
| 2018/0112239 A1 | 4/2018 | Derlot et al. |
| 2018/0179507 A1 | 6/2018 | Shibata et al. |

FOREIGN PATENT DOCUMENTS

| JP | 2011-515089 A | 5/2011 |
| JP | 2012-029678 A | 2/2012 |
| JP | 2012-75369 A | 4/2012 |
| JP | 2017-12006 A | 1/2017 |
| WO | WO 2009/117689 A1 | 9/2009 |
| WO | WO 2016/170283 A1 | 10/2016 |

OTHER PUBLICATIONS

International Search Report (ISR) for PCT/JP2018/028937; I.A. fd Aug. 1, 2018, dated Oct. 23, 2018 from the Japan Patent Office, Tokyo, Japan.
International Preliminary Report on Patentability (IPRP), Chapter I of the Patent Cooperation Treaty, including the Written Opinion, for PCT/JP2018/028937; I.A. fd Aug. 1, 2018, dated Feb. 11, 2020, by the International Bureau of WIPO, Geneva, Switzerland.
Xu, J., et al. A third xylanase from *Trichoderma reesei* PC-3-7. Appl Microbiol Biotechnol 49, 718-724 (1998). https://doi.org/10.1007/s002530051237.
Ogasawara, W. et al., "Cloning, functional expression and promoter analysis of xylanase III gene from *Trichoderma reesei*," Appl Microbiol Biotechnol. Oct. 2006;72(5):995-1003. Epub Mar. 7, 2006.
Furukawa, T. et al., "Identification of specific binding sites for XYR1, a transcriptional activator of cellulolytic and xylanolytic genes in *Trichoderma reesei*," Fungal Genet Biol. Aug. 2009;46(8):564-74. doi: 10.1016/j.fgb.2009.04.001. Epub Apr. 23, 2009.
Rauscher, R. et al., "Transcriptional regulation of xyn1, encoding xylanase I, in *Hypocrea jecorina*," Eukaryot Cell. Mar. 2006;5(3):447-56.
Hirasawa, H. et al., "Engineering of the *Trichoderma reesei* xylanase3 promoter for efficient enzyme expression," Appl Microbiol Biotechnol. Mar. 2018;102(6):2737-2752. doi: 10.1007/s00253-018-8763-5. Epub Feb. 7, 2018.
Furukawa, Takanori et al., "Analysis of transcription-activating region of xylanase III gene (xyn3) in *Trichoderma reesei* PC-3-7," Lecture Abstracts of the 2005 Annual Meeting of the Japanese Society of Applied Glycoscience and 13th Symposium on Amylases and Related Enzymes, J. Appl. Glycoscience, 2005, vol. 52, Suppl., p. 45, Abstract C3a-3.
Furukawa, Takanori et al., "Transcription-activating region existing in 5'-upstream region of *Trichoderma reesei* xyn3 gene," Lecture Abstracts of conference of the Japanese Society of Bioscience, Biotechnology and Agrochemistry, 2005, p. 28, Abstract 29D019α.

(Continued)

*Primary Examiner* — Maryam Monshipouri
(74) *Attorney, Agent, or Firm* — Sterne, Kessler, Goldstein & Fox P.L.L.C.

(57) ABSTRACT

Provision of a modified promoter derived from a xylanase promoter. A modified promoter comprising a polynucleotide of Xyn3 promoter comprising a polynucleotide that comprises at least one polynucleotide of Xyn1 promoter cis-element or a complementary strand thereof in a region corresponding to the nucleotides at position 374 to 401 of SEQ ID NO:1. The polynucleotide of Xyn3 promoter consist of the following nucleotide sequences: the nucleotide sequence represented by SEQ ID NO:1; the nucleotide sequence represented by the nucleotides at position 350 to 1084 of SEQ ID NO:1; or a nucleotide sequence that has an identity of at least 90% therewith and that comprises the sequence represented by SEQ ID NO:2 in a region corresponding to the nucleotides at position 374 to 401 of SEQ ID NO:1. The polynucleotide of Xyn1 promoter cis-element consists of the nucleotide sequence represented by SEQ ID NO:4.

20 Claims, 8 Drawing Sheets
Specification includes a Sequence Listing.

(56) References Cited

OTHER PUBLICATIONS

Furukawa, Takanori et al., "Binding specificity of *Trichoderma reesei*—derived xylanase regulator 1 (Xyr1)," Lecture Abstracts of conference of the Japanese Society of Bioscience, Biotechnology and Agrochemistry, 2008, p. 103, Abstract 2A24p19.

Li, W.-C. et al., "*Trichoderma reesei* complete genome sequence, repeat-induced point mutation, and partitioning of CAZyme gene clusters," Biotechnol Biofuels. Jul. 3, 2017;10:170. doi: 10.1186/s13068-017-0825-x. eCollection 2017, BioMed Central Open Access, 20 pages.

SEQUENCE LISTING

<160> NUMBER OF SEQ ID NOS: 43

<210> SEQ ID NO 1
<211> LENGTH: 1084
<212> TYPE: DNA
<213> ORGANISM: Trichoderma reesei PC-3-7
<220> FEATURE:
<223> OTHER INFORMATION: Xyn 3 promoter

<400> SEQUENCE: 1

```
gggaattccg tgattgacaa aatctattcg tatcaaacgt tcatgccgcc gtctccagtc    60
tcctcacgct atggtgcttg atatacataa gggggggacg ttgaatatat gttcccagtt   120
tacctccaca taagaaatat ctcctttgga cggtctctgc aattttgccc tcaagactct   180
gcagacaatc cctctgtgct ttaaaacccc cgagtatccc ggtcacctga tggcgcaagt   240
ctcaacttcc ccaggatgcc gtctcctcat ctccgtgatg gtaacaaccg catataaggg   300
acttttgtct tctttaggct tcggacgagg gggttctttc ccagatcaat gccttgaccg   360
aaactgtcaa gatggctata taggacactg tcaattttgc catttcagtc cgggtattta   420
gacttaaaag cacctagtat ttatggttaa taaatctccg ggcaaaggtc tctttccgtg   480
cgtgtctgat gggttatgct aagctcatct ccgcagacag ggtagtaaca gaggtagccg   540
ttccttggaa agacggttaa ttgacttctt gactttgact gtccaattcg catggctaat   600
tgcggcaaaa atgatgccat atggccccgt gggcacaact ttctcacaag tctctggtgt   660
cttgactgag gtcgatgttg tgctctttct tcccaactat acaagtctaa actcctcagt   720
aaatcgatac aaggtaaatt taaactctct ggttactctt cctaccaaaa ggccctggtt   780
acatttcgtg tatacccgag gcggctgaat ctgggggact cacataggtg gatgcaatgt   840
gctattagcc agctacgcat atacaatcaa acattgaaaa tcaaaggata tacaacaact   900
ttgacgattt tccataaatt ggcatcatct ttctgagtcc tgatggatgt cagacagcaa   960
gcggacaagc tggctcatga ctcaatcctc cgaatacatc gcatcatcta ggagccattc  1020
tcacctcgaa acttctacca tctttccact gagtttcaat tgaggcggac accatggaag  1080
cacc                                                              1084

<210> SEQ ID NO 2
<211> LENGTH: 28
<212> TYPE: DNA
<213> ORGANISM: Trichoderma reesei PC-3-7
<220> FEATURE:
<221> NAME/KEY: misc_feature
<222> LOCATION: (7)..(22)
<223> OTHER INFORMATION: n is a, c, g, or t

<400> SEQUENCE: 2
ggctatnnnn nnnnnnnnnn nntttgcc                                       28

<210> SEQ ID NO 3
<211> LENGTH: 28
<212> TYPE: DNA
<213> ORGANISM: Trichoderma reesei PC-3-7

<400> SEQUENCE: 3
ggctatatag gacactgtca attttgcc                                       28

<210> SEQ ID NO 4
<211> LENGTH: 22
<212> TYPE: DNA
<213> ORGANISM: Trichoderma reesei
<220> FEATURE:
<221> NAME/KEY: misc_feature
<222> LOCATION: (7)..(16)
<223> OTHER INFORMATION: n is a, c, g, or t

<400> SEQUENCE: 4
ggctaannnn nnnnnnttag cc                                             22

<210> SEQ ID NO 5
```

-continued

```
<211> LENGTH: 22
<212> TYPE: DNA
<213> ORGANISM: Trichoderma reesei

<400> SEQUENCE: 5
ggctaaatgc gacatcttag cc                                              22

<210> SEQ ID NO 6
<211> LENGTH: 34
<212> TYPE: DNA
<213> ORGANISM: Artificial
<220> FEATURE:
<223> OTHER INFORMATION: 1 Box

<400> SEQUENCE: 6
tctagaggct aaatgcgaca tcttagcctc taga                                 34

<210> SEQ ID NO 7
<211> LENGTH: 62
<212> TYPE: DNA
<213> ORGANISM: Artificial
<220> FEATURE:
<223> OTHER INFORMATION: 2 Box

<400> SEQUENCE: 7
tctagaggct aaatgcgaca tcttagcctc aagaggctaa atgcgacatc ttagcctcta     60
ga                                                                    62

<210> SEQ ID NO 8
<211> LENGTH: 62
<212> TYPE: DNA
<213> ORGANISM: Artificial
<220> FEATURE:
<223> OTHER INFORMATION: 2R Box

<400> SEQUENCE: 8
tctagaggct aagatgtcgc atttagcctc tagaggctaa gatgtcgcat ttagcctcta     60
ga                                                                    62

<210> SEQ ID NO 9
<211> LENGTH: 30
<212> TYPE: DNA
<213> ORGANISM: Artificial
<220> FEATURE:
<223> OTHER INFORMATION: xyn3-EcoRI-U

<400> SEQUENCE: 9
gggaattccg tgattgacaa aatctattcg                                      30

<210> SEQ ID NO 10
<211> LENGTH: 28
<212> TYPE: DNA
<213> ORGANISM: Artificial
<220> FEATURE:
<223> OTHER INFORMATION: xyn3-NcoI

<400> SEQUENCE: 10
ggtgcttcca tggtgtccgc ctcaattg                                        28

<210> SEQ ID NO 11
<211> LENGTH: 26
<212> TYPE: DNA
<213> ORGANISM: Artificial
<220> FEATURE:
<223> OTHER INFORMATION: xyn3P_cis_inv_Fw
```

<400> SEQUENCE: 11
agaatttcag tccgggtatt tagact                                          26

<210> SEQ ID NO 12
<211> LENGTH: 23
<212> TYPE: DNA
<213> ORGANISM: Artificial
<220> FEATURE:
<223> OTHER INFORMATION: xyn3P_cis_inv_Rv

<400> SEQUENCE: 12
agacagtttc ggtcaaggca ttg                                             23

<210> SEQ ID NO 13
<211> LENGTH: 40
<212> TYPE: DNA
<213> ORGANISM: Artificial
<220> FEATURE:
<223> OTHER INFORMATION: 1Box_Fw

<400> SEQUENCE: 13
ctgtctagag gctaagatgt cgcatttagc ctctagaatt                           40

<210> SEQ ID NO 14
<211> LENGTH: 40
<212> TYPE: DNA
<213> ORGANISM: Artificial
<220> FEATURE:
<223> OTHER INFORMATION: 1Box_Rv

<400> SEQUENCE: 14
aattctagag gctaaatgcg acatcttagc ctctagacag                           40

<210> SEQ ID NO 15
<211> LENGTH: 28
<212> TYPE: DNA
<213> ORGANISM: Artificial
<220> FEATURE:
<223> OTHER INFORMATION: xyn3-SpeI

<400> SEQUENCE: 15
ccactagtct gctacatggg tatggcag                                        28

<210> SEQ ID NO 16
<211> LENGTH: 22
<212> TYPE: DNA
<213> ORGANISM: Artificial
<220> FEATURE:
<223> OTHER INFORMATION: xyn3-EcoRI-D

<400> SEQUENCE: 16
ccgaattcaa ggcgtccctc gg                                              22

<210> SEQ ID NO 17
<211> LENGTH: 29
<212> TYPE: DNA
<213> ORGANISM: Artificial
<220> FEATURE:
<223> OTHER INFORMATION: gus-NcoI

<400> SEQUENCE: 17
cccacctata accatggtcc gtcctgtag                                       29

<210> SEQ ID NO 18

```
<210> SEQ ID NO 18
<211> LENGTH: 30
<212> TYPE: DNA
<213> ORGANISM: Artificial
<220> FEATURE:
<223> OTHER INFORMATION: gus-SpeI

<400> SEQUENCE: 18
ccactagtta ttgtttgcct ccctgctgcg                              30

<210> SEQ ID NO 19
<211> LENGTH: 45
<212> TYPE: DNA
<213> ORGANISM: Artificial
<220> FEATURE:
<223> OTHER INFORMATION: aabgl1_xyn3P

<400> SEQUENCE: 19
tgagtttcaa ttgaggcgga caatatgaag ctcagttggc ttgag            45

<210> SEQ ID NO 20
<211> LENGTH: 45
<212> TYPE: DNA
<213> ORGANISM: Artificial
<220> FEATURE:
<223> OTHER INFORMATION: aabgl1_xyn3T

<400> SEQUENCE: 20
ctgccatacc catgtagcag agcattcatt gcaccttcgg gagcg            45

<210> SEQ ID NO 21
<211> LENGTH: 39
<212> TYPE: DNA
<213> ORGANISM: Artificial
<220> FEATURE:
<223> OTHER INFORMATION: aX3invert

<400> SEQUENCE: 21
attgtccgcc tcaattgaaa ctcagtggaa agatggtag                    39

<210> SEQ ID NO 22
<211> LENGTH: 31
<212> TYPE: DNA
<213> ORGANISM: Artificial
<220> FEATURE:
<223> OTHER INFORMATION: sX3invert

<400> SEQUENCE: 22
atgctctgct acatgggtat ggcagggtcg g                            31

<210> SEQ ID NO 23
<211> LENGTH: 23
<212> TYPE: DNA
<213> ORGANISM: Artificial
<220> FEATURE:
<223> OTHER INFORMATION: recyinvert3a

<400> SEQUENCE: 23
ccgccttgtt tcagggtcga ggc                                     23

<210> SEQ ID NO 24
<211> LENGTH: 23
<212> TYPE: DNA
<213> ORGANISM: Artificial
<220> FEATURE:
<223> OTHER INFORMATION: recyinvert3s

<400> SEQUENCE: 24
```

-continued

```
gcctcgaccc tgaaacaagg cgg                                          23
```

<210> SEQ ID NO 25
<211> LENGTH: 35
<212> TYPE: DNA
<213> ORGANISM: Artificial
<220> FEATURE:
<223> OTHER INFORMATION: xyn3reps

<400> SEQUENCE: 25

```
atctcaagag tctagtatat gacggtatct ctaga                             35
```

<210> SEQ ID NO 26
<211> LENGTH: 21
<212> TYPE: DNA
<213> ORGANISM: Artificial
<220> FEATURE:
<223> OTHER INFORMATION: xyn3repa

<400> SEQUENCE: 26

```
gcctcgaccc tgaaacaagg c                                            21
```

<210> SEQ ID NO 27
<211> LENGTH: 49
<212> TYPE: DNA
<213> ORGANISM: Artificial
<220> FEATURE:
<223> OTHER INFORMATION: recyclex3s

<400> SEQUENCE: 27

```
gccgccttgt tcagggtcg aggcccaggg gacgagcccg acattaaag               49
```

<210> SEQ ID NO 28
<211> LENGTH: 50
<212> TYPE: DNA
<213> ORGANISM: Artificial
<220> FEATURE:
<223> OTHER INFORMATION: recyclex3a

<400> SEQUENCE: 28

```
aattcaaggc gtccctcggc ggcgcctcga ccctgaaaca aggcggcgac             50
```

<210> SEQ ID NO 29
<211> LENGTH: 22
<212> TYPE: DNA
<213> ORGANISM: Artificial
<220> FEATURE:
<223> OTHER INFORMATION: xyn1_2Box_inv_Rv

<400> SEQUENCE: 29

```
tctctatttc gcaggcgata ac                                           22
```

<210> SEQ ID NO 30
<211> LENGTH: 21
<212> TYPE: DNA
<213> ORGANISM: Artificial
<220> FEATURE:
<223> OTHER INFORMATION: Aabgl1_Fw

<400> SEQUENCE: 30

```
atgaagctca gttggcttga g                                            21
```

<210> SEQ ID NO 31
<211> LENGTH: 22
<212> TYPE: DNA

<213> ORGANISM: Artificial
<220> FEATURE:
<223> OTHER INFORMATION: xyn1_2box_Fw

<400> SEQUENCE: 31
gaattccgtg attgacaaaa tc                                            22

<210> SEQ ID NO 32
<211> LENGTH: 19
<212> TYPE: DNA
<213> ORGANISM: Artificial
<220> FEATURE:
<223> OTHER INFORMATION: xyn1_2box_Rv

<400> SEQUENCE: 32
atattgtccg cctcaattg                                                19

<210> SEQ ID NO 33
<211> LENGTH: 29
<212> TYPE: DNA
<213> ORGANISM: Artificial
<220> FEATURE:
<223> OTHER INFORMATION: pyr4_Fw

<400> SEQUENCE: 33
cgagttgtct agactcgact cgacttgcg                                     29

<210> SEQ ID NO 34
<211> LENGTH: 26
<212> TYPE: DNA
<213> ORGANISM: Artificial
<220> FEATURE:
<223> OTHER INFORMATION: pyr4_Rv

<400> SEQUENCE: 34
gcggaggcga gggctgttgt gcgaat                                        26

<210> SEQ ID NO 35
<211> LENGTH: 29
<212> TYPE: DNA
<213> ORGANISM: Artificial
<220> FEATURE:
<223> OTHER INFORMATION: xyn3_Fw

<400> SEQUENCE: 35
atgaaagcaa acgtcatctt gtgcctcct                                     29

<210> SEQ ID NO 36
<211> LENGTH: 36
<212> TYPE: DNA
<213> ORGANISM: Artificial
<220> FEATURE:
<223> OTHER INFORMATION: xyn3_Rv

<400> SEQUENCE: 36
ctattgtaag atgccaacaa tgctgttata tgccgg                             36

<210> SEQ ID NO 37
<211> LENGTH: 1044
<212> TYPE: DNA
<213> ORGANISM: Trichoderma reesei PC-3-7
<220> FEATURE:
<223> OTHER INFORMATION: Xyn 3 gene

<400> SEQUENCE: 37
atgaaagcaa acgtcatctt gtgcctcctg gcccccctgg tcgccgctct ccccaccgaa    60

```
accatccacc tcgaccccga gctcgccgct ctccgcgcca acctcaccga gcgaacagcc      120
gacctctggg accgccaagc tctctcaaagc atcgaccagc tcatcaagag aaaaggcaag     180
ctctactttg gcaccgccac cgaccgcggc ctcctccaac gggaaaagaa cgcggccatc      240
atccaggcag acctcggcca ggtgacgccg agaacagca tgaagtggca gtcgctcgag       300
aacaaccaag gccagctgaa ctggggagac gccgactatc tcgtcaactt tgcccagcaa      360
aacggcaagt cgatacgcgg ccacactctg atctggcact cgcagctgcc tgcgtgggtg     420
aacaatatca caacgcgga tactctgcgg caagtcatcc gcacccatgt ctctactgtg       480
gttgggcggt acaagggcaa gattcgtgct tgggacgtgg tcaatgaaat cttcaacgag      540
gatggaacgc tgcgctcttc agtctttcc aggctcctcg gcgaggagtt tgtctcgatt       600
gcctttcgtg ctgctcgaga tgctgaccct tctgcccgtc tttacatcaa cgactacaat     660
ctcgaccgcg ccaactatgg caaggtcaac gggttgaaga cttacgtctc caagtggatc     720
tctcaaggag ttcccattga cggtattgga agccagtccc atctcagcgg cggcggaggc      780
tctggtacgc tgggtgcgct ccagcagctg gcaacggtac ccgtcaccga gctggccatt     840
accgagctgg acattcaggg ggcaccgacg acgattaca cccaagttgt tcaagcatgc       900
ctgagcgtct ccaagtgcgt cggcatcacc gtgtgggca tcagtgacaa ggactcgtgg      960
cgtgccagca ccaaccctct tctgtttgac gcaaacttca ccccaagcc ggcatataac      1020 agcattgttg gcatcttaca atag                                            1044
```

<210> SEQ ID NO 38
<211> LENGTH: 347
<212> TYPE: PRT
<213> ORGANISM: Trichoderma reesei PC-3-7
<220> FEATURE:
<223> OTHER INFORMATION: Xyn 3 protein

<400> SEQUENCE: 38

```
Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
```

```
                180                 185                 190
Leu Gly Glu Glu Phe Val Ser Ile Ala Phe Arg Ala Ala Arg Asp Ala
                195                 200                 205

Asp Pro Ser Ala Arg Leu Tyr Ile Asn Asp Tyr Asn Leu Asp Arg Ala
            210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
            290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345
```

```
<210> SEQ ID NO 39
<211> LENGTH: 1215
<212> TYPE: DNA
<213> ORGANISM: Penicillium sp.
<220> FEATURE:
<223> OTHER INFORMATION: PspXyn gene

<400> SEQUENCE: 39
atggtttgct tgtctaccaa agcactgctc ctcggagctg ccactctacc acagcttgtt      60
cactctgcgg tcttgacac agctgctgta gctcttggaa agaaatactt cggaactgcc     120
acagataatc agagttgac cgatacagca tacgtggccc agctgaacaa caccaggac     180
ttcggccaga tcacacctgg aaattctcag aagtgggatg ctaccgagcc gtcacaaaac     240
acgttcacct tcacgaatgg cgacgtgatt gctgatctgg ctgaagctaa cggccaaaag     300
ctgcgatgcc acaatcttgt gtggtatgaa cagctaccta gctgggtttc agcggaacc     360
tggaccaacg caaccctcct cgcagcgatg aagaaccata taccaacgt cgtgactcac     420
tacaagggac agtgctacgc ctgggacgtt gtcaatgaag gtctcaacga cgacggaaca     480
taccgtgaca acatcttcta ccaatacatt ggtgaagcat acatcccaat gcctttgcg     540
acagccgctg ccgccgaccc gagcgtcaag ctctactata cgactacaa catcgagtcc     600
gcaggagcca agtccaccgc tgcgcaaaac atcgtcaagc tggtcaagtc ataccggtgtc     660
aagatcgatg gtgttggtct ccaatctcac ttcattgttg aagcacacc cagccagagc     720
gcacaggcta gcaacatggc tgcgtttact gctctcggcg tcgaggtcgc tattactgag     780
ttggatatcc gtatgacctt gccctctacc gatgctttgc tcgcccagca aagacagac     840
tatgcgagca ccgttgccgc ttgtgcgcaa acgagcggct gcgttggtat cacgatctgg     900
gactggacgg acaagtactc atgggtcccg aacactttct ctggacaggg tgcggcatgc     960
ccgtgggatg cgaacttggt gaagaagcca gcttataccg gcatcttgac tgcgctgggt    1020
ggtactgcca cgagcaccgc cacgacaact gcaaagacta ccttgactac tagcaccacc    1080
tcatctgggt cctctagtac gagtgttgcg cagaagtggg ggcaatgcgg tggtagtggc    1140
```

```
tggaccggac caacgacttg tgtcagtggc accacctgca cctactccaa tgcttggtac    1200
tcgcaatgtc tttga                                                     1215
```

<210> SEQ ID NO 40
<211> LENGTH: 404
<212> TYPE: PRT
<213> ORGANISM: Penicillium sp.
<220> FEATURE:
<223> OTHER INFORMATION: PspXyn

<400> SEQUENCE: 40

```
Met Val Cys Leu Ser Thr Lys Ala Leu Leu Gly Ala Ala Thr Leu
1               5                   10                  15

Pro Gln Leu Val His Ser Ala Gly Leu Asp Thr Ala Ala Val Ala Leu
            20                  25                  30

Gly Lys Lys Tyr Phe Gly Thr Ala Thr Asp Asn Pro Glu Leu Thr Asp
        35                  40                  45

Thr Ala Tyr Val Ala Gln Leu Asn Asn Thr Gln Asp Phe Gly Gln Ile
    50                  55                  60

Thr Pro Gly Asn Ser Gln Lys Trp Asp Ala Thr Glu Pro Ser Gln Asn
65                  70                  75                  80

Thr Phe Thr Phe Thr Asn Gly Asp Val Ile Ala Asp Leu Ala Glu Ala
                85                  90                  95

Asn Gly Gln Lys Leu Arg Cys His Asn Leu Val Trp Tyr Glu Gln Leu
            100                 105                 110

Pro Ser Trp Val Ser Ser Gly Thr Trp Thr Asn Ala Thr Leu Leu Ala
        115                 120                 125

Ala Met Lys Asn His Ile Thr Asn Val Val Thr His Tyr Lys Gly Gln
    130                 135                 140

Cys Tyr Ala Trp Asp Val Val Asn Glu Gly Leu Asn Asp Asp Gly Thr
145                 150                 155                 160

Tyr Arg Asp Asn Ile Phe Tyr Gln Tyr Ile Gly Glu Ala Tyr Ile Pro
                165                 170                 175

Ile Ala Phe Ala Thr Ala Ala Ala Asp Pro Ser Val Lys Leu Tyr
            180                 185                 190

Tyr Asn Asp Tyr Asn Ile Glu Ser Ala Gly Ala Lys Ser Thr Ala Ala
        195                 200                 205

Gln Asn Ile Val Lys Leu Val Lys Ser Tyr Gly Val Lys Ile Asp Gly
    210                 215                 220

Val Gly Leu Gln Ser His Phe Ile Val Gly Ser Thr Pro Ser Gln Ser
225                 230                 235                 240

Ala Gln Ala Ser Asn Met Ala Ala Phe Thr Ala Leu Gly Val Glu Val
                245                 250                 255

Ala Ile Thr Glu Leu Asp Ile Arg Met Thr Leu Pro Ser Thr Asp Ala
            260                 265                 270

Leu Leu Ala Gln Gln Lys Thr Asp Tyr Ala Ser Thr Val Ala Ala Cys
        275                 280                 285

Ala Gln Thr Ser Gly Cys Val Gly Ile Thr Ile Trp Asp Trp Thr Asp
    290                 295                 300

Lys Tyr Ser Trp Val Pro Asn Thr Phe Ser Gly Gln Gly Ala Ala Cys
305                 310                 315                 320

Pro Trp Asp Ala Asn Leu Val Lys Lys Pro Ala Tyr Thr Gly Ile Leu
                325                 330                 335

Thr Ala Leu Gly Gly Thr Ala Thr Ser Thr Ala Thr Thr Thr Ala Lys
```

```
                         340                 345                 350
Thr Thr Leu Thr Thr Ser Thr Thr Ser Ser Gly Ser Ser Ser Thr Ser
            355                 360                 365

Val Ala Gln Lys Trp Gly Gln Cys Gly Gly Ser Gly Trp Thr Gly Pro
        370                 375                 380

Thr Thr Cys Val Ser Gly Thr Thr Cys Thr Tyr Ser Asn Ala Trp Tyr
385                 390                 395                 400

Ser Gln Cys Leu

<210> SEQ ID NO 41
<211> LENGTH: 90
<212> TYPE: DNA
<213> ORGANISM: Artificial
<220> FEATURE:
<223> OTHER INFORMATION: 3 Box

<400> SEQUENCE: 41
tctagaggct aaatgcgaca tcttagcctc ttgaggctaa atgcgacatc ttagcctctt      60
gaggctaaat gcgacatctt agcctctaga                                       90

<210> SEQ ID NO 42
<211> LENGTH: 90
<212> TYPE: DNA
<213> ORGANISM: Artificial
<220> FEATURE:
<223> OTHER INFORMATION: 3R Box

<400> SEQUENCE: 42
tctagaggct aagatgtcgc atttagcctc aagaggctaa gatgtcgcat ttagcctcaa      60
gaggctaaga tgtcgcattt agcctctaga                                       90

<210> SEQ ID NO 43
<211> LENGTH: 174
<212> TYPE: DNA
<213> ORGANISM: Artificial
<220> FEATURE:
<223> OTHER INFORMATION: 6R Box

<400> SEQUENCE: 43
tctagaggct aagatgtcgc atttagcctc aagaggctaa gatgtcgcat ttagcctcaa      60
gaggctaaga tgtcgcattt agcctcaaga ggctaagatg tcgcatttag cctcaagagg    120
ctaagatgtc gcatttagcc tcaagaggct aagatgtcgc atttagcctc taga           174
```

MODIFIED PROMOTER

FIELD OF THE INVENTION

The present invention relates to a modified promoter and a method for producing the same, and a vector and a transformant containing the modified promoter.

BACKGROUND OF THE INVENTION

Techniques for producing sugars from cellulose in biomass materials (hereinafter referred to as "biomass") and converting the sugars into fuels and chemicals such as ethanol by fermentation or the like are known. With respect to this technology, various technological developments have been made against the background of interest in environmental problems in recent years, and large-scale production of fuels and chemicals using this technology has also begun to be developed.

Biomass is composed of cellulose fibers, and hemicellulose and lignin containing mainly xylan surrounding the cellulose fibers. In the production of sugars using biomass as a raw material, enzymes for hydrolyzing cellulose and hemicellulose are required. Saccharification of biomass by cellulase, and enzymatic degradation of biomass by hemicellulase and ligninase have been performed conventionally. For example, Patent Document 1 discloses an enzymatic composition for converting biomass to sugars, containing cellulase, hemicellulase such as Trichoderma reesei-derived xylanase and arabinofuranosidase. Patent Document 2 discloses a method for producing sugar including reacting a protein having xylanase activity derived from a group of microorganisms present in bagasse compost and cellulase with a biomass resource.

Trichoderma reesei, a filamentous fungus, is a fungus that efficiently produces xylanase and is conventionally used for production of xylanase. Three xylanases (Xyn1, Xyn2 and Xyn3) have been reported to date as xylanases derived from Trichoderma reesei. Of these xylanases, Xyn1 and Xyn2 are classified into glycoside hydrolase family 11: GH11, while Xyn3 is classified into glycoside hydrolase family 10: GH10 and belongs to a family different from Xyn1 and Xyn2. Xyn3 is highly expressed only in PC-3-7 strain among several Trichoderma reesei mutants derived from the Trichoderma reesei QM9414 strain. The expression level of Xyn3 in the PC-3-7 strain is higher than that of the other two xylanases Xyn1 and Xyn2.

Xyn3 is also expressed by a regulatory mechanism distinct from Xyn1 and Xyn2. Expression of Xyn1 and Xyn2 is induced by xylan and cellulose, whereas expression of Xyn3 is not induced by xylan (an enzyme substrate), but by cellulose and its derivatives (Non-Patent Documents 1 and 2). In order to elucidate an expression regulatory mechanism of these xylanases, the promoters of these genes have been analyzed. As a region essential for expression of Xyn3, a cis-element composed of binding domains (5'-GGCTAT-3' and 5'-GGCAAA-3') of Xyr1 (a transcriptional regulator essential for producing lignocellulase) and a 16 bp-spacer sequence on a promoter region of a gene encoding Xyn3 has been reported (Non-Patent Document 3). On the other hand, as a region essential for expression of Xyn1, a cis-element composed of a Xyr1 binding domain (5'-GGCTAA-3') and a 10-bp spacer sequence on a promoter region of a gene encoding Xyn1 has been reported (Non-Patent Document 4). Thus, although cis-elements of the Xyn1 promoter and the Xyn3 promoter have similar structures each other, their inducers differ. The reasons for the different responses of the cis-elements to cellulose and xylan between these promoters are unclear.

(Patent Document 1) JP-A-2011-515089
(Patent Document 2) JP-A-2012-029678
(Non-Patent Document 1) Appl Microbiol Biotechnol, 1998, 49:718-724
(Non-Patent Document 2) Appl Microbiol Biotechnol, 2006, 72:995-1003
(Non-Patent Document 3) Fungal Genet Biol, 2009, 46(8): 564-574
(Non-Patent Document 4) Eukaryot Cell, 2006, 5(3):447-456

SUMMARY OF THE INVENTION

In one aspect, the present invention provides a modified promoter, comprising:

a polynucleotide of Xyn3 promoter comprising a polynucleotide that comprises at least one polynucleotide of Xyn1 promoter cis-element or a complementary strand thereof in a region corresponding to the nucleotides at position 374 to 401 of SEQ ID NO:1, wherein the polynucleotide of the Xyn3 promoter is the following:

a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 90% with the nucleotide sequence represented by SEQ ID NO:1 or the nucleotide sequence represented by the nucleotides at position 350 to 1084 of SEQ ID NO:1, and comprises the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose;

wherein the polynucleotide of Xyn1 promoter cis-element consists of the nucleotide sequence represented by GGCTAA-NNNNNNNNNN-TTAGCC (SEQ ID NO:4); and wherein the polynucleotide that comprise at least one polynucleotide of Xyn1 promoter cis-elements or a complementary strand thereof does not comprise HAP2/3/5 binding site and CREI binding site.

In another embodiment, the present invention provides a vector comprising the above-described modified promoter.

In another embodiment, the present invention provides a DNA fragment comprising a gene of interest and the modified promoter upstream of the gene.

In another embodiment, the invention provides a transformant comprising the vector or the DNA fragment.

In a further embodiment, the present invention provides a method of producing a modified promoter; comprising substituting or inserting a polynucleotide that comprises at least one polynucleotide of Xyn1 promoter cis-element or a complementary strand thereof into a region corresponding to the nucleotides at position 374 to 401 of SEQ ID NO: 1 in a polynucleotide of Xyn3 promoter, wherein the polynucleotide of Xyn3 promoter is the following:

a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 90% with the nucleotide sequence represented by SEQ ID NO:1 or the nucleotide sequence represented by the nucleotides at position 350 to 1084 of SEQ ID NO:1, and comprises the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose;

wherein the polynucleotide of Xyn1 promoter cis-element consists of the nucleotide sequence represented by GGCTAA-NNNNNNNNNN-TTAGCC (SEQ ID NO:4); and wherein the polynucleotide that comprises at least one polynucleotide of Xyn1 promoter cis-element or a complementary strand thereof does not comprise HAP2/3/5 binding site and CREI binding site.

DETAILED DESCRIPTION OF THE INVENTION

Figure 1:
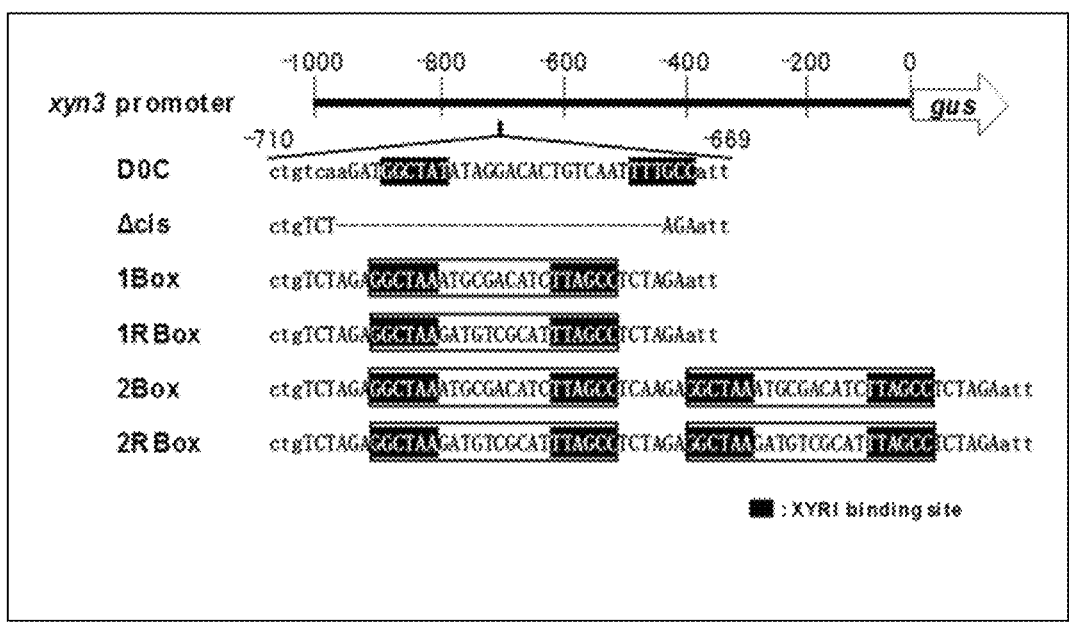
FIG. 1 shows the sequence of region contained in the modified promoter in the GUS reporter cassette produced in Example 2. Black frame: Xyn1 promoter cis-element, white characters on a black background: XYRI binding site.

All patent, non-patent, and other publications cited herein are incorporated by reference in their entirety.

In the specification, nucleotide sequence identity and amino acid sequence identity are calculated in accordance with the Lipman-Pearson method (Science, 1985, 227: 1435-1441). More specifically, they were calculated by analysis using genetic information processing software, Genetyx-Win homology (Search homology) analysis program, assuming that the unit size to compare (ktup) is specified to 2.

In the specification, "identity of at least 90%" with respect to an amino acid sequence or nucleotide sequence refers to an identity of 90% or more, preferably 95% or more, more preferably 96% or more, still more preferably 97% or more, still more preferably 98% or more, and still more preferably 99% or more. Also in the specification, "identity of at least 95%" with respect to an amino acid sequence or nucleotide sequence refers to an identity of 95% or more, preferably 96% or more, more preferably 97% or more, still more preferably 98% or more, and still more preferably 99% or more.

In the specification, the "corresponding position" or "corresponding region" on an amino acid sequence or nucleotide sequence can be determined by aligning a sequence of interest and a reference sequence (e.g., the nucleotide sequence represented by SEQ ID NO:1) to provide maximum homology. Alignment of an amino acid sequence or a nucleotide sequence can be performed using known algorithms, and the procedures are known to those skilled in the art. For example, alignment can be performed by using Clustal W multiple alignment program (Thompson, J. D. et al, 1994, Nucleic Acids Res. 22:4673-4680) as the default setting. Alternatively, a revised version of the Clustal W, such as Clustal W2 or Clustal omega, can be used. Clustal W, Clustal W2 and Clustal omega are available, for example, on the website of the European Bioinformatics Institute: ebi.ac.uk/index.html and the DNA Data bank of Japan (DDBJ: ddbj.nig.ac.jp/searches-i.html) managed by the National Institute of Genetics. The position or region of the sequence of interest aligned with any region of the reference sequence by the alignment described above is considered to be a "corresponding position" or "corresponding region" in any such region.

In the specification, "upstream" and "downstream" with respect to a gene refers to upstream and downstream in the direction of transcription of the gene. For example, "a gene located downstream of a promoter" means that the gene is present 3' to the promoter in the DNA sense strand, and upstream of the gene means the region 5' to the gene in the DNA sense strand.

In the specification, an "operable ligation" between a promoter and a gene means that the promoter is ligated so as to induce transcription of the gene. Procedures for "operable ligating" between a promoter and a gene are well known to those skilled in the art.

In the specification, "promoter activity" means activity that promotes expression of a gene located downstream thereof, and more particularly, activity that promotes transcription of a gene located downstream thereof from DNA to mRNA. Promoter activity can be confirmed by using an appropriate reporter gene. For example, promoter activity can be confirmed by ligating a DNA encoding a detectable protein, i.e., a reporter gene, downstream of a promoter and measuring the amount of the expression product of the reporter gene. Examples of the reporter gene include β-galactosidase (LacZ) gene, β-glucuronidase (GUS) gene, luciferase gene, β-lactamase gene, gene for fluorescent proteins such as GFP (Green Fluorescent Protein) gene, and the like. Alternatively, the promoter activity can be confirmed by measuring the amount of mRNA transcribed from a reporter gene by a quantitative RT-PCR or the like.

In the specification, the term "native" used for a function, property, or trait of a cell is used to indicate that the function, property, or trait is originally present in the cell. In contrast, the term "foreign" is used to indicate that the function, property, or trait is not originally present in the cell, but introduced externally thereto. For example, a "foreign" gene or polynucleotide refers to a gene or polynucleotide introduced externally into a cell. The foreign gene or polynucleotide may be derived from the same types of organism as the cell into which the gene or polynucleotide was introduced or derived from a heterologous organism, (i.e., a heterologous gene or polynucleotide).

In the specification, a "Xyn3 promoter" refers to the promoter of a gene encoding xylanase Xyn3, and an equivalent promoter thereto. Examples of the Xyn3 promoter include a promoter consisting of the following polynucleotides:

a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 90% with the nucleotide sequence represented by SEQ ID NO:1 or the nucleotide sequence represented by the nucleotides at position 350 to 1084 of SEQ ID NO:1, and contains the sequence represented by GGCTAT-NNNNNNNNNNNNNNNN-TTTGCC (SEQ ID NO:2, N represents any nucleotide) in a region corresponding to the nucleotides at position 374 to 401 of SEQ ID NO:1, and having promoter activity induced by cellulose.

Preferred examples of the nucleotide sequence that has an identity of at least 90% with the nucleotide sequence represented by SEQ ID NO:1 include the nucleotide sequence represented by the nucleotides at position 3 to 1073 of SEQ ID NO:1. Preferred examples of the nucleotide sequence that has an identity of at least 90% with the nucleotide sequence represented by the nucleotides at position 350 to 1084 of SEQ ID NO:1 include the nucleotide sequence represented by the nucleotides at position 350 to 1073 of SEQ ID NO:1. These sequences include the sequence represented by GGCTAT-NNNNNNNNNNNNNNNN-TTTGCC (SEQ ID NO:2; N is any nucleotide) in a region corresponding to the nucleotides at position 372 to 399 of SEQ ID NO:1, and have promoter activity induced by cellulose. Thus, further examples of the Xyn3 promoter of the present invention include a promoter consisting of the following polynucleotides:

a polynucleotide consisting of the nucleotide sequence represented by the nucleotides at position 3 to 1073 of SEQ ID NO:1;

a polynucleotide consisting of the nucleotide sequence represented by the nucleotides at position 350 to 1073 of SEQ ID NO:1; or a polynucleotide consisting of a nucleotide sequence that has an identity of at least 90% with the nucleotide sequence represented by the nucleotides at position 3 to 1073 of SEQ ID NO:1, or the nucleotide sequence represented by the nucleotides at position 350 to 1073 of SEQ ID NO:1, and contains the sequence represented by GGCTAT-NNNNNNNNNNNNNNNN-TTTGCC (SEQ ID NO:2; N is any nucleotide) in a region corresponding to the nucleotides at position 374 to 401 of SEQ ID NO:1, and having promoter activity induced by cellulose.

The GGCTAT-NNNNNNNNNNNNNNNN-TTTGCC (SEQ ID NO:2) is a Xyn3 promoter cis-element. Preferred examples of the sequence represented by SEQ ID NO:2 include the sequence represented by GGCTATATAGGACACTGTCAATTTTGCC (SEQ ID NO:3).

Preferably, the Xyn3 promoter carries a motif possessed by the existing xylanase promoter (Non-Patent Document 2: Fungal Genet Biol, 2008, 45:1094-1102). Examples of such motif include TATA box, CREI binding site, ACEI binding site, ACEII binding site, and CAAT motif. More particularly, the following regions are included:

TATA box (e.g., TATA) in a region corresponding to the nucleotides at position 860 to 863 and 889-892 of SEQ ID NO:1;

CREI binding site in a region corresponding to the nucleotides at position 53 to 58, the nucleotides at position 124 to 129, the nucleotides at position 249 to 254, the nucleotides at position 456 to 461, the nucleotides at position 509 to 514, and the nucleotides at position 811 to 816 of SEQ ID NO:1 (e.g., a sequence selected from the group consisting of CTCCAG, CTCCAC, CCCCAG, CTCCGG, CTCCGC and CTGGGG);

ACEI binding site in a region corresponding to the nucleotides at position 350 to 354 of SEQ ID NO:1 (e.g., TGCCT, AGGCA);

ACEII binding site in a region corresponding to the nucleotides at position 594 to 599 and the nucleotide position 845 to 850 of SEQ ID NO:1 (e.g., a sequence selected from the group consisting of GGCTAA, TTAGCC and GGCTAA); and CAAT motif in a region corresponding to the nucleotides at position 583 to 587 of SEQ ID NO:1 (e.g., CCAAT).

In the specification, a "Xyn1 promoter cis-element" refers to a cis-element present on the promoter of a gene encoding xylanase Xyn1, and an equivalent cis-element thereto. Examples of the Xyn1 promoter cis-element include a polynucleotide consisting of the nucleotide sequence represented by GGCTAA-NNNNNNNNNN-TTAGCC (SEQ ID NO:4; N is any nucleotide). Preferred examples of the sequence represented by SEQ ID NO:4 include the sequence represented by GGCTAAATGCGACATCTTAGCC (SEQ ID NO:5).

The present invention relates to a modified promoter derived from a xylanase promoter and a method for producing the same. The present invention also relates to a provision of a vector and a transformant containing the modified promoter.

The present inventors have found that modification of a promoter cis-element of a gene encoding xylanase Xyn3 based on a cis-element of another xylanase promoter enhances expression inducibility of the promoter of the gene encoding Xyn3 in biomass.

The modified promoter of the present invention has improved inducibility in response to sophorose and cellulose, and may have inducibility in response to a xylan substance. According to the present invention, it is possible to improve efficiency of microbiological production of xylanase and other enzymes involved in degradation or saccharification of biomass.

The present invention provides a modified promoter. The modified promoter of the present invention is a modified promoter of the Xyn3 promoter. Typically, the modified promoter of the present invention has been obtained by substituting or inserting a polynucleotide containing a Xyn1 promoter cis-element or a complementary strand thereof with respect to the cis-element region of the polynucleotide of the Xyn3 promoter. The Xyn3 promoter is a parent promoter of the modified promoter of the present invention.

In the present invention, substitution or insertion of a cis-element (or a complementary strand thereof) consisting of a predetermined nucleotide sequence or a polynucleotide containing the same into a Xyn3 promoter is performed such that the predetermined nucleotide sequence (or a complementary strand thereof) is located on the strand of the promoter that is ligated to the DNA-sense strand. Similarly, when the modified promoter of the present invention contains a cis-element (or a complementary strand thereof) consisting of a predetermined nucleotide sequence, or a polynucleotide containing the same, the predetermined nucleotide sequence (or complementary strand thereof) is present on the strand of the promoter that is linked to the DNA-sense strand.

In a preferred embodiment, the present invention is a modified promoter, containing:

a polynucleotide of Xyn3 promoter containing a polynucleotide that contains at least one polynucleotide of Xyn1 promoter cis-element or a complementary strand thereof in a region corresponding to the nucleotides at position 374 to 401 of SEQ ID NO:1, wherein the polynucleotide of Xyn3 promoter is the following:

a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 90% with the nucleotide sequence represented by SEQ ID NO:1, or the nucleotide sequence represented by the nucleotides at position 350 to 1084 of SEQ ID NO:1 and contains the sequence represented by GGCTAT-NNNNNNNNNNNNNNNN-TTTGCC (SEQ ID NO 2) in a region corresponding to the nucleotides at position 374 to 401 of SEQ ID NO:1, and having promoter activity induced by cellulose, and wherein the polynucleotide of Xyn1 promoter cis-element consists of the nucleotide sequence represented by GGCTAA-NNNNNNNNNN-TTAGCC (SEQ ID NO:4).

In a preferred embodiment, the polynucleotide of Xyn3 promoter is a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 95% with the nucleotide sequence represented by SEQ ID NO:1, or the nucleotide sequence represented by the nucleotides at position 350 to 1084 of SEQ ID NO:1 and contains the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose.

In a more preferred embodiment, the polynucleotide of Xyn3 promoter is a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 95% with the nucleotide sequence represented by SEQ ID NO:1, or the nucleotide sequence represented by the nucleotides at position 350 to 1084 of SEQ ID NO:1 and contains the sequence represented by GGCTATATAGGACACTGTCAATTTTGCC (SEQ ID NO:3) in a region corresponding to the nucleotides at position 374 to 401 of SEQ ID NO:1, and having promoter activity induced by cellulose.

In a further preferred embodiment, the polynucleotide of Xyn3 promoters is a polynucleotide consisting of the nucleotide sequence represented by the nucleotides at position 3 to 1073 of SEQ ID NO:1;

a polynucleotide consisting of the nucleotide sequence represented by the nucleotides at position 350 to 1073 of SEQ ID NO:1; or a polynucleotide consisting of a nucleotide sequence that has an identity of at least 90% with the nucleotides at position 3 to 1073 of SEQ ID NO:1, or the nucleotide sequence represented by the nucleotides at position 350 to 1073 of SEQ ID NO:1 and contains the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose. In a further preferred embodiment, the sequence represented by GGCTAT-NNNNNNNNNNNNNNNN-TTTGCC (SEQ ID NO:2) is the sequence represented by GCTATATAGGACACTGT-CAATTTTGCC (SEQ ID NO:3).

In a further preferred embodiment, the polynucleotide of Xyn3 promoters is a polynucleotide consisting of the nucleotide sequence represented by the nucleotides at position 3 to 1073 of SEQ ID NO:1;

a polynucleotide consisting of the nucleotide sequence represented by the nucleotides at position 350 to 1073 of SEQ ID NO:1; or a polynucleotide consisting of a nucleotide sequence that has an identity of at least 95% with the nucleotide sequence represented by the nucleotides at position 3 to 1073 of SEQ ID NO:1, or the nucleotide sequence represented by the nucleotides at position 350 to 1073 of SEQ ID NO:1 and contains the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose. In a further preferred embodiment, the sequence GGCTAT-NNNNNNNNNNNNNNNN-TTTGCC (SEQ ID NO:2) is the sequence GCTATATAGGACACTGT-CAATTTTGCC (SEQ ID NO:3).

In a preferred embodiment, the polynucleotide of Xyn1 promoter cis-element consists of the nucleotide sequence represented by GGCTAAATGCGACATCTTAGCC (SEQ ID NO:5).

In the modified promoter of the present invention, the polynucleotide that comprises at least one polynucleotide of Xyn1 promoter cis-element or a complementary strand thereof (also referred to as a "Xyn1 cis-element-containing fragment" in the following specification) may be substituted or inserted into a region corresponding to the nucleotides at position 374-401 of SEQ ID NO:1 (also referred to as a "374-401 region" in the following specification) in the polynucleotide of Xyn3 promoter (parent promoter). The number of the Xyn1 cis-elements or complementary strands thereof contained in the Xyn1 cis-element-containing fragment is preferably 1 to 10, more preferably 1 to 8, further preferably 1 to 6, further preferably 2 to 6, and further preferably 1, 2, 3 or 6.

In a preferred embodiment, the Xyn1 cis-element-containing fragment is a polynucleotide containing 1 to 10, more preferably 1 to 8, further preferably 1 to 6, further preferably 2 to 6, and further preferably 1, 2, 3 or 6 polynucleotides consisting of the nucleotide sequence represented by SEQ ID NO:4, or complementary strands thereof. Thus, in a preferred embodiment, the modified promoter of the present invention contains 1 to 10, more preferably 1 to 8, further preferably 1 to 6, further preferably 2 to 6, and further preferably 1, 2, 3 or 6 polynucleotides consisting of the nucleotide sequence represented by SEQ ID NO:4, or complementary strands thereof.

In a further preferred embodiment, the Xyn1 cis-element-containing fragment is a polynucleotide containing 1 to 10, more preferably 1 to 8, further preferably 1 to 6, further preferably 2 to 6, and further preferably 1, 2, 3 or 6 polynucleotides consisting of the nucleotide sequence represented by SEQ ID NO:5. In another further preferred embodiment, the Xyn1 cis-element-containing fragment is a polynucleotide containing 1 to 10, more preferably 1 to 8, further preferably 1 to 6, further preferably 2 to 6, and further preferably 1, 2, 3 or 6 complementary strands of a polynucleotide consisting of the nucleotide sequence represented by SEQ ID NO:5. In a still preferred embodiment, the Xyn1 cis-element-containing fragment is a polynucleotide containing two polynucleotides consisting of the nucleotide sequence SEQ ID NO:5, or a polynucleotide containing one or two complementary strands of a polynucleotide consisting of the nucleotide sequence represented by SEQ ID NO:5. In another still preferred embodiment, the Xyn1 cis-element-containing fragment is a polynucleotide containing three polynucleotides consisting of the nucleotide sequence SEQ ID NO:5, or a polynucleotide containing three or six complementary strands of a polynucleotide consisting of the nucleotide sequence represented by SEQ ID NO:5.

When the Xyn1 cis-element-containing fragment contains two or more polynucleotides consisting of the nucleotide sequence represented by SEQ ID NO:4 or 5, or complementary strands thereof, the fragment preferably has a spacer sequence between each of them. The spacer sequence may be any sequence consisting of 5 to 20 bases as long as it does not inhibit the gene expression regulatory function of the Xyn1 cis-element-containing fragment. Examples of such spacer sequence include TCAAGA, TCTAGA and the like.

Thus, preferred examples of the Xyn1 cis-element-containing fragment include a polynucleotide consisting of two or more, preferably 2 to 10, more preferably 2 to 8, further preferably 2 to 6, further preferably 3 to 6, and further preferably 2, 3 or 6 repeats of the nucleotide sequence represented by SEQ ID No:5 or a complementary strand thereof or a sequence in which the spacer sequence is ligated downstream of the nucleotide sequence represented by SEQ ID NO:5 or a complementary strand thereof. These Xyn1 cis-element-containing fragments may have the above-mentioned spacer sequences located at the most upstream and the most downstream thereof.

Preferred examples of the Xyn1 cis-element-containing fragment are as follows:

a polynucleotide consisting of the nucleotide sequence represented by SEQ ID NO:6 or a complementary strand thereof;

a polynucleotide consisting of the nucleotide sequence represented by SEQ ID NO:7;

a polynucleotide consisting of the nucleotide sequence represented by SEQ ID NO:8;

a polynucleotide consisting of the nucleotide sequence represented by SEQ ID NO:41;

a polynucleotide consisting of the nucleotide sequence represented by SEQ ID NO:42; and a polynucleotide consisting of the nucleotide sequence represented by represented by SEQ ID NO:43.

Thus, in a preferred embodiment, the modified promoter of the present invention contains the following polynucleotide in the 374-401 region in contrast to the Xyn3 promoter (parent promoter):

a polynucleotide consisting of the nucleotide sequence represented by SEQ ID NO:6 or its complement;

a polynucleotide consisting of the nucleotide sequence represented by SEQ ID NO:7;

a polynucleotide consisting of the nucleotide sequence represented by SEQ ID NO:8;

a polynucleotide consisting of the nucleotide sequence represented by SEQ ID NO:41;

a polynucleotide consisting of the nucleotide sequence represented by SEQ ID NO:42; or, a polynucleotide comprising the nucleotide sequence represented by SEQ ID NO:43.

The promoter of Xyn1 gene has HAP2/3/5 binding site (transcriptional promoter, 5'-CCAAT-3') and CREI binding site (carbonaceous catabolic inhibitor, 5'-SYGGRG-3', 5'-CCCCAG-3') adjacent to a cis-element thereof (Biosci Biotechnol Biochem, 2016, 80 (9):1712-1729). On the other hand, the Xyn1 cis-element-containing fragment which is substituted or inserted into the parent promoter preferably does not contain the HAP2/3/5 binding site and CREI binding site. Also preferably, the modified promoter of the present invention does not include HAP2/3/5 binding site and CREI binding site in the vicinity of the cis-element of the substituted or inserted Xyn1 promoter. When the Xyn1 cis-element-containing fragment that does not contain HAP2/3/5 binding site and CREI binding site is substituted or inserted into the 374-401 region of the Xyn3 promoter, the HAP2/3/5 binding site and CREI binding site are not located in the vicinity of the cis-element of the substituted or inserted Xyn1 promoter. It has been reported that when the Xyn1 promoter cis-element containing HAP binding site or CREI binding site was substituted or inserted, the promoter activity of the modified promoter was reduced (Applied Microbiology and Biotechnology, 2018, 102(6):2737-2752).

When producing the modified promoter of the present invention from the parent promoter, the entire 374-401 region of the Xyn3 promoter may be substituted with the Xyn1 cis-element-containing fragment, or the Xyn1 cis-element-containing fragment may be inserted in the region, leaving all of the nucleotides of the 374-401 region. Alternatively, the Xyn1 cis-element-containing fragment may be inserted in the 374-401 region so as to substitute a part of the 374-401 region with the Xyn1 cis-element-containing fragment. In other words, in the modified promoter of the present invention, the 374-401 region may be deleted in their entirety, or apart thereof, or may be interrupted by the Xyn1 cis-element-containing fragment. Preferably, in the modified promoter of the present invention, the entire 374-401 region of the Xyn3 promoter is substituted with the Xyn1 cis-element-containing fragment, and the entire 374-401 region is deleted.

A method for obtaining the modified promoter of the present invention is not particularly limited, and the modified promoter can be obtained by a conventional chemical synthesis method or a genetic engineering method. For example, the modified promoter of the present invention can be artificially synthesized. For artificial synthetic of DNA, for example, services of such as Invitrogen Corporation or the like can be used. Alternatively, the modified promoter of the present invention can be produced by genetically engineering the Xyn3 promoter.

The parent promoter of the modified promoter of the present invention may be artificially synthesized by the means described above, or may be cloned from a microorganism. For example, the polynucleotide of the Xyn3 promoter consisting of the nucleotide sequence represented by SEQ ID NO:1 can be cloned from the *Trichoderma reesei* PC-3-7 strain.

Alternatively, the parent promoter of the modified promoter of the present invention can be cloned from a *Trichoderma reesei* PC-3-7 strain to which a mutation is introduced. For example, a mutation may be introduced into the DNA of a Xyn3 promoter in the *Trichoderma reesei* PC-3-7 strain, and a polynucleotide consisting of a nucleotide sequence that has an identity of at least 90% with the nucleotide sequence represented by SEQ ID NO:1 and contains the sequence represented by SEQ ID NO:2 in a region corresponding to the nucleotides at position 374 to 401 of SEQ ID NO:1 and having promoter activity may be selected from the obtained mutant DNA. Examples of the mutation method include ultraviolet irradiation and site-directed mutagenesis. The promoter activity of the mutant DNA can be measured, for example, by operably ligating a gene of interest downstream of the mutant DNA and analyzing the expression amount of the target gene. The introduction of a mutation and selection of the mutant DNA of interest is a routine matter of those skilled in the art.

The substitution or insertion of Xyn1 cis-element-containing fragment into the 374-401 region of the parent promoter can be made according to procedures well known to those skilled in the art, such as fragment construction by use of PCR and ligation. For example, upstream and downstream fragments of the 374-401 region of the parent promoter (Xyn3 promoter) and a Xyn1 cis-element-containing fragment can be prepared by using PCR, and they are ligated together to place the Xyn1 cis-element-containing fragment between the upstream and downstream fragments to thereby prepare a DNA fragment containing the modified promoter of the present invention, which contains the Xyn1 cis-element-containing fragment in place of the 374-401 region.

The modified promoter of the present invention has a function of regulating expression of the gene located downstream thereof. By utilizing the modified promoter of the present invention, a DNA fragment having an expression regulatory region excellent in transcriptional activity can be obtained. For example, a DNA fragment can be constructed containing a gene of interest and a modified promoter of the invention operably ligated upstream thereof. Alternatively, a DNA fragment containing the modified promoter of the present invention can be constructed to have restriction enzyme recognition sequences at both ends. The restriction enzyme recognition sequence can be used to introduce the modified promoter of the present invention into a vector. That is, the modified promoter of the present invention can be introduced into a vector by cleaving a known vector with a restriction enzyme and adding thereto a DNA fragment containing the modified promoter of the present invention and having a restriction enzyme-cleaving sequence at the end thereof (restriction enzyme method).

Thus, the modified promoters of the present invention can be contained in a vector. By incorporating the modified promoter of the present invention into a vector capable of expressing a gene of interest, an expression vector capable of improving the expression of the gene of interest at the transcriptional level can be obtained. In the expression vector, the modified promoter of the present invention may be operably ligated upstream of the DNA encoding the gene of interest. The vector having the promoter of the present invention may be either in a form that is introduced into a chromosome of a host cell or held extrachromosomally. Alternatively, a DNA fragment having the gene of interest and a modified promoter of the invention operably ligated upstream thereof may be constructed and introduced directly into the genome of the host cell.

The vector incorporating the modified promoter of the present invention is not particularly limited as long as it can be stably maintained and propagated in a host cell, and examples thereof include a plasmid containing AMA1 that acts as an autonomous replicating factor in *Aspergillus* microorganism.

The modified promoter of the present invention has improved promoter activity inducibility by cellulose or a derivative thereof, which is possessed by the Xyn3 promoter of the parent promoter. Preferably, it further acquires promoter activity inducibility by xylan or a derivative thereof. Thus, the modified promoter of the present invention is suitable for use in an environment where cellulose and xylan are present. For example, the modified promoter of the present invention is suitable as a promoter of an enzyme used in a process of decomposition or saccharification of biomass.

Therefore, the gene of interest operably ligated to the modified promoter of the present invention in the vector or DNA fragment containing the promoter is preferably a gene encoding an enzyme used in the process of biomass degradation or biomass saccharification, for example, cellulase (e.g., β-endoglucanase, cellobiohydrolase, β-glucosidase, etc.), hemicellulase (e.g., endoxylanase, β-xylosidase, arabinofuranosidase, glucuronidase, acetylxylan esterase, mannase, β-mannosidase, ferulic acid esterase, etc.), a xylanase, and the like. Alternatively, the gene of interest is preferably a gene regulated by a promoter which does not originally induce expression by cellulose or xylan. More preferred examples of the gene of interest operably ligated to the modified promoter of the present invention include a polynucleotide encoding xylanase Xyn3 consisting of the amino acid sequence represented by SEQ ID NO:38; a polynucleotide encoding xylanase consisting of an amino acid sequence having an identity of at least 90% with SEQ ID NO:38; a polynucleotide encoding a xylanase consisting of the nucleotide sequence represented by SEQ ID NO:37 or consisting of a nucleotide sequence having an identity of at least 90% therewith, and the like. Another preferred examples of the gene of interest include a polynucleotide encoding xylanase PspXyn consisting of the amino acid sequence represented by SEQ ID NO:40 (WO2016/208492); a polynucleotide encoding xylanase consisting of an amino acid sequence having an identity of at least 90% with SEQ ID NO:40; a polynucleotide encoding a xylanase consisting of the nucleotide sequence represented by SEQ ID NO:39 or consisting of a nucleotide sequence having an identity of at least 90% therewith. However, the types of the gene of interest that can be operably ligated to the promoter of the present invention are not limited thereto.

The transformant (transformed cell) of the present invention can be obtained by introducing a vector or DNA fragment containing the modified promoter of the present invention into a host cell using a general transformation method such as electroporation, transformation, transfection, conjugation, protoplast, particle gun method, and *Agrobacterium* method.

Examples of a host cell into which the vector or DNA fragment is introduced include, but are not limited to, eukaryotes, preferably fungi, more preferably filamentous fungi, as long as the promoter of the present invention can function as a promoter in the cell. Preferred filamentous fungi include, for example, filamentous fungi of the genus *Acremonium*, the genus *Aspergillus*, the genus *Aureobasidium*, the genus *Bjerkandera*, the genus *Ceriporiopsis*, the genus *Chrysosporium*, the genus *Ceriporiopsis*, the genus *Coprinus*, the genus *Coriolus*, the genus *Cryptococcus*, the genus *Filibasidium*, the genus *Fusarium*, the genus *Humicola*, the genus *Magnaporthe*, the genus *Mucor*, the genus *Myceliophthora*, the genus *Neocallimastix*, the genus *Neurospora*, the genus *Paecilomyces*, the genus *Penicillium*, the genus *Phanerochaete*, the genus *Phlebia*, the genus *Piromyces*, the genus *Pleurotus*, the genus *Rhizopus*, the genus *Schizophyllum*, the genus *Talaromyces*, the genus *Thermoascus*, the genus *Thielavia*, the genus *Tolypocladium*, the genus *Trametes* and the genus *Trichoderma*; and among them, filamentous fungi of the genus *Trichoderma* are preferred, and *Trichoderma reesei* and a mutant strain thereof are more preferred. Examples of *Trichoderma reesei* and a mutant strain thereof include the *Trichoderma reesei* QM9414 strain and a mutant strain thereof, e.g. *Trichoderma reesei* PC-3-7 strain.

The following materials, manufacturing methods, uses, methods, and the like are further disclosed herein as exemplary embodiments of the present invention. However, the present invention is not limited to these embodiments.

[1] A modified promoter, comprising:
a polynucleotide of Xyn3 promoter comprising a polynucleotide that comprises at least one polynucleotide of Xyn1 promoter cis-element or a complementary strand thereof in a region corresponding to the nucleotides at position 374 to 401 of SEQ ID NO:1,
wherein the polynucleotide of Xyn3 promoter is the following:
a polynucleotide consisting of the nucleotide sequence represented by SEQ ID NO:1;
a polynucleotide consisting of the nucleotide sequence represented by the nucleotides at position 350 to 1084 of SEQ ID NO:1; or
a polynucleotide consisting of a nucleotide sequence that has an identity of at least 90% with the nucleotide sequence represented by SEQ ID NO:1, or the nucleotide sequence represented by the nucleotides at position 350 to 1084 of SEQ ID NO:1 and that comprises the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose,
wherein the polynucleotide of Xyn1 promoter cis-element consists of the nucleotide sequence represented by GGCTAA-NNNNNNNNNN-TTAGCC (SEQ ID NO:4) and
wherein the polynucleotide that comprises at least one polynucleotide of Xyn1 promoter cis-element or a complementary strand thereof does not comprise HAP2/3/5 binding site and CREI binding site.

[2] The modified promoter according to [1], wherein the polynucleotide of Xyn3 promoter comprises:
preferably one or more selected from the group consisting of TATA box, CREI binding site, ACEI binding site, ACEII binding site, and CAAT motif; and
more preferably TATA box, CREI binding site, ACEI binding site, ACEII binding site, and CAAT motif.

[3] The modified promoter according to [2], wherein the TATA box is preferably TATA box in a region corresponding to the nucleotides at position 860 to 863 and 889 to 892 of SEQ ID NO:1 (e.g., TATA).

[4] The modified promoter according to [2] or [3], wherein the CREI binding site is
preferably CREI binding site in a region corresponding to the nucleotides at position 456 to 461, the nucleotides at position 509 to 514, and the nucleotides at position 811 to 816 of SEQ ID NO:1 (e.g., a sequence selected from the group consisting of CTCCAG, CTCCAC, CCCCAG, CTCCGG, CTCCGC and CTGGGG); and
more preferably CREI binding site in a region corresponding to the nucleotides at position 53 to 58, the nucleotides at position 124 to 129, the nucleotides at position 249 to 254, the nucleotides at position 456 to 461, the nucleotides at position 509 to 514, and the nucleotides at position 811 to 816 of SEQ ID NO:1 (e.g., a sequence selected from the group consisting of CTCCAG, CTCCAC, CCCCAG, CTCCGG, CTCCGC and CTGGGG).

[5] The modified promoter according to any one of [2] to [4], wherein the ACEI binding site is preferably TGCCT or AGGCA in a region corresponding to the nucleotides at position 350 to 354 of SEQ ID NO:1.

[6] The modified promoter according to any one of [2] to [5], wherein the ACEII binding site is preferably ACEII binding site in a region corresponding to the nucleotides at position 594 to 599 and 845 to 850 of SEQ ID NO:1 (e.g., a sequence selected from the group consisting of GGCTAA, TTAGCC and GGCTAA).

[7] The modified promoter according to any one of [2] to [6], wherein the CAAT motif is preferably CAAT motif in a region corresponding to the nucleotides at position 583 to 587 (e.g., CCAAT).

[8] The modified promoter according to any one of [1] to [7], wherein the polynucleotide of Xyn3 promoter is preferably the following:
a polynucleotide consisting of the nucleotide sequence represented by SEQ ID NO:1;
a polynucleotide consisting of the nucleotide sequence represented by the nucleotides at position 350 to 1084 of SEQ ID NO:1; or
a polynucleotide consisting of a nucleotide sequence that has an identity of at least 95% with the nucleotide sequence represented by SEQ ID NO:1, or the nucleotide sequence represented by the nucleotides at position 350 to 1084 of SEQ ID NO:1 and that comprises the sequence represented by SEQ ID NO:2 in a region corresponding to the nucleotides at position 374 to 401 of SEQ ID NO:1, and having promoter activity induced by cellulose.

[9] The modified promoter according to any one of [1] to [7], wherein the polynucleotide of Xyn3 promoter is preferably the following:
a polynucleotide consisting of the nucleotide sequence represented by the nucleotides at position 3 to 1073 of SEQ ID NO:1;
a polynucleotide consisting of the nucleotide sequence represented by the nucleotides at position 350 to 1073 of SEQ ID NO:1; or
a polynucleotide consisting of the nucleotide sequence that has an identity of at least 90% with the nucleotide sequence represented by the nucleotides at position 3 to 1073 of SEQ ID NO:1 or the nucleotide sequence represented by the nucleotides at position 350 to 1073 of SEQ ID NO:1, and that comprises the sequence represented by the SEQ ID NO:1 in a region corresponding to the nucleotides at position 374 to 401 of SEQ ID NO:1, and having promoter activity induced by cellulose.

[10] The modified promoter according to any one of [1] to [9], wherein the nucleotide sequence comprising the sequence represented by SEQ ID NO:2 is preferably a sequence represented by GGCTATATAGGACACTGT-CAATTTTGCC (SEQ ID NO:3).

[11] The modified promoter according to any one of [1] to [10], wherein the polynucleotide that comprises at least one polynucleotide of Xyn1 promoter cis-element or a complementary strand thereof preferably comprises 1 to 10, more preferably 1 to 8, further preferably 1 to 6, further preferably 2 to 6, and further preferably 1, 2, or 6 polynucleotides consisting of the nucleotide sequence represented by SEQ ID NO:4.

[12] The modified promoter according to [11], wherein the polynucleotide consisting of the nucleotide sequence represented by SEQ ID NO:4 is preferably a polynucleotide consisting of the nucleotide sequence represented by SEQ ID NO:5.

[13] The modified promoter according to any one of [1] to [12], wherein the polynucleotide that comprises at least one polynucleotide of Xyn1 promoter cis-element or a complementary strand thereof preferably does not comprise HAP2/3/5 binding site and CREI binding site, and
the HAP2/3/5 junction site is CCAAT and the CREI binding site is SYGGRG or CCCCAG.

[14] The modified promoter according to any one of [1] to [13], wherein the polynucleotide that comprises at least one polynucleotide of Xyn1 promoter cis-element or a complementary strand thereof is preferably a polynucleotide consisting of two or more, more preferably 2 to 10, further preferably 2 to 8, further preferably 2 to 6, further preferably 3 to 6, and further preferably 2, 3 or 6 repeats of the nucleotide sequence represented by SEQ ID No:5 or a complementary strand thereof or a sequence in which the spacer sequence is ligated downstream of the nucleotide sequence represented by SEQ ID NO:5 or a complementary strand thereof.

[15] The modified promoter according to [14], wherein the spacer sequence is preferably TCAAGA or TCTAGA.

[16] The modified promoter according to any one of [1 to [15], wherein the polynucleotide that comprises at least one polynucleotide of Xyn1 promoter cis-element or a complementary strand thereof is preferably the following:
a polynucleotide consisting of the nucleotide sequence represented by SEQ ID NO:6 or a complementary strand thereof;
a polynucleotide consisting of the nucleotide sequence represented by SEQ ID NO:7;
a polynucleotide consisting of the nucleotide sequence represented by SEQ ID NO:8;
a polynucleotide consisting of the nucleotide sequence represented by SEQ ID NO:41;
a polynucleotide consisting of the nucleotide sequence represented by SEQ ID NO:42; or,
a polynucleotide consisting of the nucleotide sequence represented by SEQ ID NO:43.

[17] The modified promoter according to any one of [1] to [16], wherein preferably the entirety of or a part of the region corresponding to the nucleotides at position 374 to 401 of SEQ ID NO:1 is deleted, or the region corresponding to the nucleotides at position 374 to 401 of SEQ ID NO:1 is interrupted by the polynucleotide comprising the polynucleotide of at least one Xyn1 promoter cis-element or a complementary strand thereof.

[18] A method for producing a modified promoter, comprising:
substituting or inserting a polynucleotide that comprises at least one polynucleotide of Xyn1 promoter cis-element or a complementary strand thereof into a region corresponding to the nucleotides at position 374 to 401 of SEQ ID NO: 1 in polynucleotide of a Xyn3 promoter,
wherein the polynucleotide of Xyn3 promoter is the following:
a polynucleotide consisting of the nucleotide sequence represented by SEQ ID NO:1;
a polynucleotide consisting of the nucleotide sequence represented by the nucleotides at position 350 to 1084 of SEQ ID NO:1; or
a polynucleotide consisting of a nucleotide sequence that has an identity of at least 90% with the nucleotide sequence represented by SEQ ID NO:1, or the nucleotide sequence represented by the nucleotides at position 350 to 1084 of SEQ ID NO:1 and that comprises the sequence represented by GGCTAT-NNNNNNNNNNNNNNNN-TTTGCC (SEQ ID NO:2) in a region corresponding to the nucleotides at position 374 to 401 of SEQ ID NO:1, and having promoter activity induced by cellulose,
wherein the polynucleotide of Xyn1 promoter cis-element consists of the nucleotide sequence represented by GGCTAA-NNNNNNNNNN-TTAGCC (SEQ ID NO:4) and
wherein the polynucleotide that comprises at least one polynucleotide of Xyn1 promoter cis-element or a complementary strand thereof does not comprise HAP2/3/5 binding site and CREI binding site.

[19] The method according to [18], wherein the polynucleotide of Xyn3 promoter comprises:
preferably one or more selected from the group consisting of TATA box, CREI binding site, ACEI binding site, ACEII binding site, and CAAT motif; and
more preferably TATA box, CREI binding site, ACEI binding site, ACEII binding site, and CAAT motif.

[20] The method according to [19], wherein the TATA box is preferably TATA box in a region corresponding to the nucleotides at position 860 to 863 and 889 to 892 of SEQ ID NO:1 (e.g., TATA).

[21] The method according to [19] or [20], wherein the CREI binding site is
preferably CREI binding site in a region corresponding to the nucleotides at position 456 to 461, the nucleotides at position 509 to 514, and the nucleotides at position 811 to 816 of SEQ ID NO:1 (e.g., a sequence selected from the group consisting of CTCCAG, CTCCAC, CCCCAG, CTCCGG, CTCCGC and CTGGGG); and
more preferably CREI binding site in a region corresponding to the nucleotides at position 53 to 58, the nucleotides at position 124 to 129, the nucleotides at position 249 to 254, the nucleotides at position 456 to 461, the nucleotides at position 509 to 514, and the nucleotides at position 811 to 816 of SEQ ID NO:1 (e.g., a sequence selected from the group consisting of CTCCAG, CTCCAC, CCCCAG, CTCCGG, CTCCGC and CTGGGG).

[22] The method according to any one of [19] to [21], wherein the ACEI binding site is preferably TGCCT or AGGCA in a region corresponding to the nucleotides at position 350 to 354 of SEQ ID NO:1.

[23] The method according to any one of [19] to [22], wherein the ACEII binding site is preferably ACEII binding site in a region corresponding to the nucleotides at position 594 to 599 and 845 to 850 of SEQ ID NO:1 (e.g., a sequence selected from the group consisting of GGCTAA, TTAGCC and GGCTAA).

[24] The method according to any one of [19] to [23], wherein the CAAT motif is preferably CAAT motif in a region corresponding to the nucleotides at position 583 to 587 (e.g., CCAAT).

[25] The method according to any one of [18] to [24], wherein the polynucleotides of Xyn3 promoter is preferably the following:

a polynucleotide consisting of the nucleotide sequence represented by SEQ ID NO:1;

a polynucleotide consisting of the nucleotide sequence represented by the nucleotides at position 350 to 1084 of SEQ ID NO:1; or a polynucleotide consisting of a nucleotide sequence that has an identity of at least 95% with the nucleotide sequence represented by SEQ ID NO:1, or the nucleotide sequence represented by the nucleotides at position 350 to 1084 of SEQ ID NO:1 and that comprises the sequence represented by SEQ ID NO:2 in a region corresponding to the nucleotides at position 374 to 401 of SEQ ID NO:1, and having promoter activity induced by cellulose.

[26] The method according to any one of [18 to [24], wherein the polynucleotides of Xyn3 promoter is preferably the following:

a polynucleotide consisting of the nucleotide sequence represented by the nucleotides at position 3 to 1073 of SEQ ID NO:1;

a polynucleotide consisting of the nucleotide sequence represented by the nucleotides 350 to 1073 of SEQ ID NO:1; or a polynucleotide consisting of a nucleotide sequence that has an identity of at least 90% with the nucleotide sequence represented by the nucleotides at position 3 to 1073 of SEQ ID NO:1, or the nucleotide sequence represented by the nucleotides at position 350 to 1084 of SEQ ID NO:1 and that comprises the sequence represented by SEQ ID NO:2 in a region corresponding to the nucleotides at position 374 to 401 of SEQ ID NO:1, and having promoter activity induced by cellulose.

[27] The method according to any one of [18] to [26], wherein the nucleotide sequence comprising the sequence represented by SEQ ID NO:2 is preferably a sequence represented by GGCTATATAGGACACTGTCAAT-TTTGCC (SEQ ID NO:3).

[28] The method according to any one of [18] to [27], wherein the polynucleotides that comprises at least one polynucleotide of Xyn1 promoter cis-element or a complementary strand thereof preferably comprises 1 to 10, more preferably 1 to 8, further preferably 1 to 6, further preferably 2 to 6, and further preferably 1, 2, 3 or 6 of polynucleotides consisting of the nucleotide sequence represented by SEQ ID NO:4 or a complementary strand thereof.

[29] The method according to [28], wherein the polynucleotide consisting of the nucleotide sequence represented by SEQ ID NO:4 is preferably a polynucleotide consisting of the nucleotide sequence represented by SEQ ID NO:5.

[30] The method according to any one of [18] to [29], wherein preferably the polynucleotide that comprises at least one polynucleotide of Xyn1 promoter cis-element or a complementary strand thereof does not preferably comprise HAP2/3/5 binding site and CREI binding site, and the HAP2/3/5 binding site is CCAAT and the CREI binding site is SYGGRG or CCCCAG.

[31] The method according to any one of [18] to [30], wherein the polynucleotide that comprises at least one polynucleotide of Xyn1 promoter cis-element or a complementary strand thereof is preferably a polynucleotide consisting of two or more, more preferably 2 to 10, further preferably 2 to 8, further preferably 2 to 6, further preferably 3 to 6, and further preferably 2, 3 or 6 repeats of the nucleotide sequence represented by SEQ ID No:5 or a complementary strand thereof or a sequence in which the spacer sequence is ligated downstream of the nucleotide sequence represented by SEQ ID NO:5 or a complementary strand thereof.

[32] The method according to [31], wherein the spacer sequence is preferably TCAAGA or TCTAGA.

[33] The method according to any one of [18] to [32], wherein the polynucleotide that comprises at least one polynucleotide of Xyn1 promoter cis-element or a complementary strand thereof is preferably the following:

a polynucleotide consisting of the nucleotide sequence represented by SEQ ID NO:6 or a complementary strand thereof;

a polynucleotide consisting of the nucleotide sequence represented by SEQ ID NO:7;

a polynucleotide consisting of the nucleotide sequence represented by SEQ ID NO:8;

a polynucleotide consisting of the nucleotide sequence represented by SEQ ID NO:41;

a polynucleotide consisting of the nucleotide sequence represented by SEQ ID NO:42; or, a polynucleotide consisting of the nucleotide sequence represented by SEQ ID NO:43.

[34] The method according to any one of [18] to [33], wherein the polynucleotide that comprises at least one polynucleotide of Xyn1 promoter cis-element or a complementary strand thereof is substituted with the entire or a part of the region corresponding to the nucleotides at position 374 to 401 of SEQ ID NO:1, or inserted into the region corresponding to the nucleotides at position 374 to 401 of SEQ ID NO:1.

[35] A vector comprising the modified promoter according to any one of [1] to [17].

[36] The vector according to [35], wherein the modified promoter is preferably ligated upstream of a gene of interest.

[37] The vector according to [36], wherein the gene of interest is preferably a gene encoding an enzyme selected from the group consisting of cellulase, hemicellulase, and cellulase, more preferably a polynucleotide encoding xylanase consisting of the nucleotide sequence represented by SEQ ID NO:37 or consisting of a nucleotide sequence having an identity of at least 90% therewith or a polynucleotide encoding xylanase consisting of the nucleotide sequence represented by SEQ ID NO:39 or consisting of a nucleotide sequence having an identity of at least 90% therewith.

[38] A DNA fragment comprising a gene of interest and the modified promoter according to any one of [1] to [17] ligated upstream of the gene.

[39] The DNA fragment according to [38], wherein the gene of interest is preferably a gene encoding an enzyme selected from the group consisting of cellulase, hemicellulase, and cellulase, more preferably a polynucleotide encoding xylanase consisting of the nucleotide sequence represented by SEQ ID NO:37 or consisting of a nucleotide sequence having an identity of at least 90% therewith or a polynucleotide encoding xylanase consisting of the nucleotide sequence represented by SEQ ID NO:39 or consisting of a nucleotide sequence having an identity of at least 90% therewith.

[40] A transformant comprising the vector according to any one of [35] to [37] or the DNA fragment according to [38] or [39].
[41] The transformant according to [40], which is the genus *Trichoderma*.

EXAMPLE

Hereinafter, the present invention will be explained in more detail on the basis of examples, but the present invention is not limited thereto.

Example 1 Preparation of Modified Xyn3 Promoter (1) Cloning of Xyn3 Promoter

A Xyn3 promoter region (SEQ ID NO:1) containing primer fragments at both ends was amplified by PCR using a gene region including upstream of a gene (xyn3) encoding a xylanase Xyn3 derived from the *Trichoderma reesei* PC-3-7 strain as a template, and using primer xyn3-EcoRI-U (SEQ ID NO:9) and primer xyn3-NcoI (SEQ ID NO:10). The resulting fragment was introduced into pT7blue (Novagen) and plasmid pTxyn3PD0 was obtained. For reporter cassette construction, plasmid pTxyn3PD0 was cleaved with BamHI and XbaI to obtain a DNA fragment containing the amplified promoter region, and the DNA fragment was introduced into pKF18K plasmid (Takara) to obtain Xyn3 promoter-containing plasmid pKFxyn3PD0.

(2) Removal of Cis-Element from Xyn3 Promoter

In the pKFxyn3PD0, the Xyn3 promoter cis-element (SEQ ID NO:3) was removed and XbaI restriction enzyme site was added by PCR using primer xyn3P_cis_inv_Fw (SEQ ID NO:11) and primer xyn3P_cis_inv_Rv (SEQ ID NO:12). Plasmid pKFxyn3β-Δcis was obtained by self-ligation of the PCR product.

(3) Preparation of Xyn1 Promoter Cis-Element-Containing Fragment

A DNA fragment containing the cis-element of the promoter of the gene encoding Xyn1 (SEQ ID NO:5) was constructed. A DNA fragment (1Box; SEQ ID NO: 6) containing one sequence represented by SEQ ID NO:5 and XbaI sites at both ends, and a complementary strand thereof (1RBox) were constructed from the gene region including upstream of the gene (xyn1) encoding xylanase Xyn1 derived from *Trichoderma reesei* PC-3-7 strain, using primer 1Box_Fw (SEQ ID NO:13) and primer 1Box_Rv (SEQ ID NO:14). In addition, DNA fragments (2Box and 2RBox; SEQ ID NOs: 7 and 8) containing two of the sequences represented by SEQ ID NO:5 or complementary strands thereof and containing XbaI sites at both ends were synthesized.

(4) Preparation of Modified Xyn3 Promoter-Containing Plasmid

Each of the DNA fragments produced in (3) was introduced into the pKFxyn3β-Δcis which has been cleaved with XbaI, to construct modified promoter-containing plasmids pKFxyn3-1Box, pKFxyn3-1RBox, pKFxyn3-2Box and pKFxyn3-2RBox.

Example 2 Preparation of Modified Promoter-Containing Reporter Cassette (1) Preparation of GUS Reporter-Containing Plasmid In order to evaluate the inducibility of the modified Xyn3 promoter produced in Example 1, a reporter cassette in which a gene (gus) encoding a reporter GUS (β-glucuronidase) was introduced under the regulation of each promoter. Into the pT7Blue-T (Novagen), a 0.8 kbp xyn3 downstream region amplified using primer xyn3-SpeI (SEQ ID NO:15) and primer xyn3-EcoRI-D (SEQ ID NO:16) were introduced to obtain a pTxyn3T. The gus gene was amplified using primer gus-NcoI (SEQ ID NO:17) and primer gus-SpeI (SEQ ID NO:18) using pBACgus-1 (Novagen) as a template, and the gus gene was introduced into a pT7Blue-T, thereby obtaining a pTgus-1. The pTxyn3T and pTgus-1 were cleaved by SpeI and ligated to construct a pTgus-2 (which has xyn3 downstream region after stop codon of gus gene).

(2) Preparation of Promoter-GUS Fragment

The pKFxyn3PD0, pKFxyn3β-Δcis and the modified promoter-containing plasmid produced in Example 1 were cleaved with BamHI and NcoI to obtain a DNA fragment. The pTgus-2 produced in (1) was cleaved with BamHI and NcoI to obtain a DNA fragment. The pKFxyn3PD0 fragment and pTgus-2 fragment were ligated to prepare plasmid pTxyn3-PD0. The pKFxyn3β-Δcis fragment and pTgus-2 fragment were ligated to prepare plasmid pTxyn3-Δcis. The modified promoter-containing plasmid fragment and pTgus-2 fragment were ligated to prepare plasmids pTxyn3-1Box, pTxyn3-2Box, pTxyn3-1RBox and pTxyn3-2RBox, respectively. The resulting plasmids were cleaved with EcoRI and NsiI, respectively, to obtain a fragment containing the promoter-GUS.

(3) Preparation of Xyn3-amdS Fragment

A 7.7 kbp of DNA fragment containing xyn3 ORF (containing a 3.1 kbp of xyn3 upstream region, a 1.4 kbp of xyn3 ORF, and a 3.2 kbp of xyn3 downstream region) was cloned from the *Trichoderma reesei* PC-3-7 strain. pBluescript II SK (Novagen) was cleaved with EcoRI followed by blunting, to construct pBEs (lacking EcoRI site). The pBE was cleaved by SalI and ligated with the 7.7 kbp of fragment described above to obtain pBxyn3S'. This plasmid was partially cleaved with EcoRI and blunted to construct a pBxyn3SE' in which only EcoRI site existing in the downstream region was deleted. p3SR2 (Mol Cell Biol, 1983, 3(8):1430-1439) was cleaved with SpeI and XbaI to obtain a 3.5 kbp of a DNA fragment containing amdS gene (including the *Aspergillus nidulans* acetoamidase gene amdS and its upstream and downstream regions). The pBxyn3SE' was cleaved with Nan and ligated to the 3.5 kbp of DNA fragment to obtain pBxyn3amdS. The resulting plasmid was cleaved with coRI and NsiI to obtain a fragment containing xyn3-amdS.

(4) Preparation of GUS Reporter Cassette for Promoter Analysis

The promoter-GUS fragment produced in (2) was introduced into the xyn3-amdS fragment produced in (3), to prepare plasmids containing the GUS reporter cassette for promoter analysis, pBxyn3ag-DOC, pBxyn3ag-Δcis, pBxyn3ag-1Box, pBxyn3ag-1RBox, pBxyn3ag-2Box, and pBxyn3ag-2RBox. The sequences of the modified Xyn3 promoter, gus gene, and amdS gene were confirmed using Genome Lab™ (Dye Terminator Cycle Sequencing Quick Start kit) and CEQ™ M 2000XL DNA sequencer (Beckman Coulter) for the obtained plasmids. The sequence of the cis-element region contained in the modified promoter in the prepared reporter cassette is shown in FIG. 1.

Example 3 Preparation of Transformant and Evaluation of Inducibility of Promoter (1) Acquisition of Transformant A transformant with a reporter cassette containing the modified promoter prepared in Example 2 was prepared.

First, the GUS reporter cassette-containing plasmid prepared in (4) of Example 2 was cleaved with SalI. The resulting fragment was introduced into the *Trichoderma reesei* PC-3-7 strain by the protoplast PEG method (Biotechnol Bioeng, 2012, January; 109(1):92-99).

A transformant was selected using a selection medium with acetamide as a single nitrogen source (2% (w/v) glucose, 0.6 mg/mL $MgSO_4$, 0.6 mg/mL $CaCl_2$, 12.5 mM $CsCl_2$, 10 mM $KH_2PO_4$ Buffer (pH 5.5), 0.005 mg/mL $FeSO_4.7H_2O$, 0.00 16 mg/mL $MnSO_4.H_2O$, 0.0014 mg/mL $ZnSO_4.7H_2O$, 0.002 mg/mL $CoCl_2$, 2% (w/v) agar). Selected transformant candidate strains were cultured twice in minimal medium supplemented with acetamide and stabilized. Homologous recombination and introduced copies in a transformant were confirmed by southern analysis using AlkPhos Direct kit (GE Healthcare Bio Science, Waukesha, Wis.). As a result, it was confirmed that the reporter cassette was homologously recombined by one copy at the position of the xyn3 gene on the genome. Transformants introduced with pBxyn3ag-DOC, pBxyn3ag-Δcis, pBxyn3ag-1Box, pBxyn3ag-1RBox, pBxyn3ag-2Box, and pBxyn3ag-2RBox were obtained as DOC strain, Δcis strain, 1Box strain, 1RBox strain, 2Box strain, and 2RBox strain, respectively.

(2) Preparation of Liquid Extract of Cells and Measurement of GUS Activity

The conidia of $1×10^6$ transformants were cultured in 50 mL of 0.3% (w/v) glucose-containing culture medium at 28° C. and 220 rpm for 48 h, and the cells were collected by filtration. The collected cells were transferred to and cultured in 50 mL of an induction medium with an inducer to the promoter as a single carbon source (0.0075% (w/v) $CaCl_2.2H_2O$, 0.0075% (w/v) $MgSO_4.7H_2O$, 0.025% (w/v) Tween80, 0.025% (w/v) Trace element, 50 mM citrate buffer (pH 4.0). As an inducer, either of 0.1% (w/v) glucose, 0.05% (w/v) sorbose, 0.01% (w/v) sophorose, 0.1% (w/v) xylose, or 0.1% (w/v) birch wood xylan was used.

* 1) Trace element composition: 0.006% (w/v) $H_3BO_3$, 0.026% (w/v) $(NH_4)6Mo_7O_24.4H_2O$, 0.1% (w/v) $FeCl_3.6H_2O$, 0.4% (w/v) $CuSO_4.5H_2O$, 0.008% (w/v) $MnCl_2.4H_2O$, 0.2% (w/v) $ZnCl_2$ After 12 h of induction, the mycelia were collected using miracloth and immediately frozen in liquid nitrogen. The frozen mycelia were powdered using a multibead shocker, suspended in GUS liquid extract (50 mM sodium phosphate buffer, 10 mM EDTA (pH 8.0), 10 mM β-mercaptoethanol, 0.1% (w/v) TritonX, 0.1% (w/v) sodium lauroyl sarcosinate), and centrifuged at 13,000×g, for 15 min, at 4° C. The obtained supernatant was used as a GUS liquid extract. The β-glucuronidase (GUS) activity and the protein amount in the GUS liquid extract were measured, and the GUS activity per protein amount was determined. The GUS activity was quantified by reacting GUS with 4-methylumbelliferyl-β-D-glucuronide (4-MUG) as a substrate at 37° C. for 10 min and then measuring the fluorescence. The protein amount was quantified by the Bradford method using bovine immunoglobulin as a standard.

(3) Results

Figure 2:
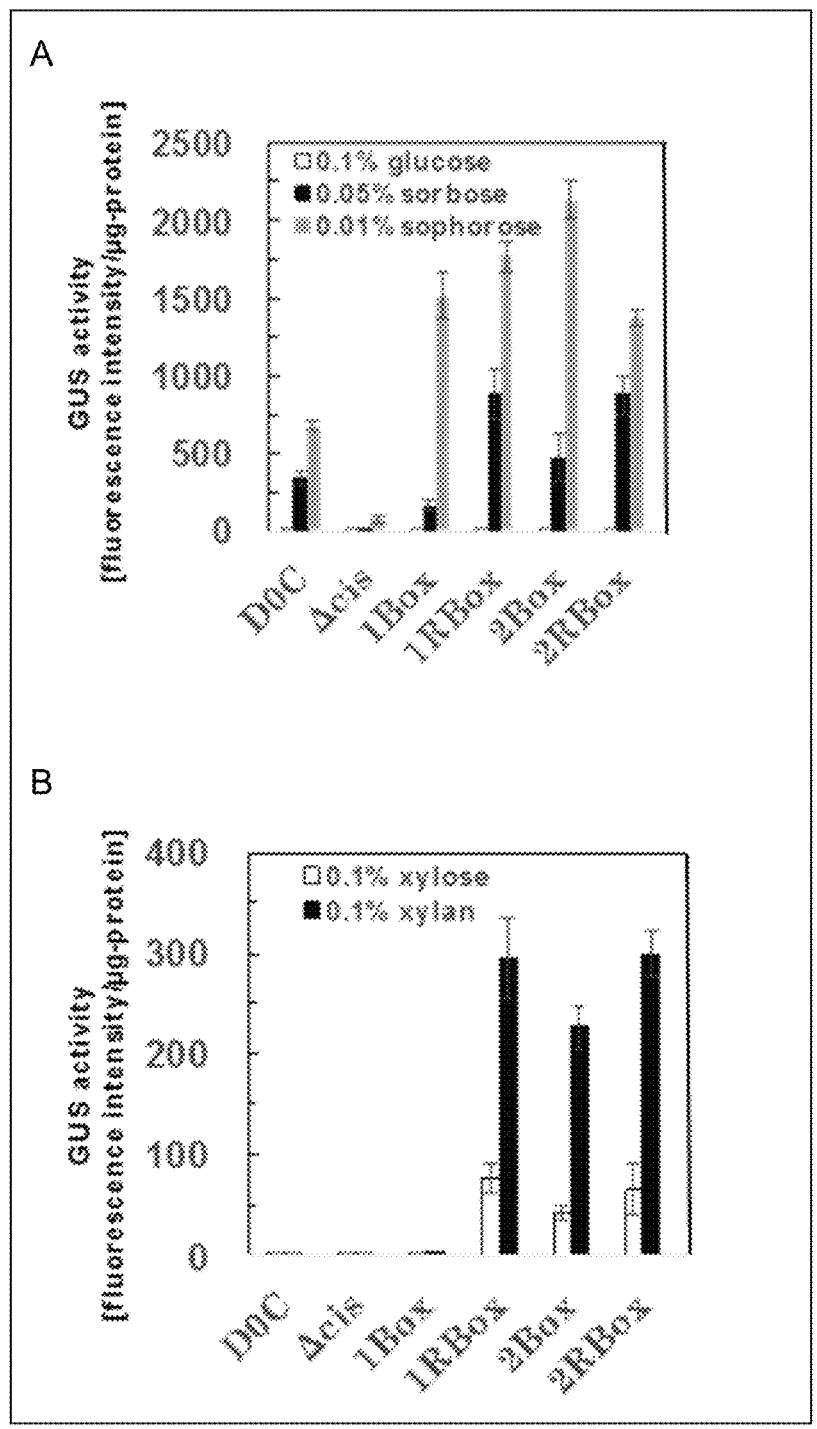
FIG. 2 shows GUS activity in the liquid extract of modified promoter-introduced cells after 12-hour induction culture. A: GUS activity after culture in the presence of glucose, sorbose or sophorose. B: GUS activity after culture in the presence of xylose or xylan.

The measurement results of GUS activity are shown in FIG. 2. FIG. 2A shows GUS activity in liquid extracts of cells cultured in the presence of glucose, sorbose, or sophorose, a cellulosic substrate. In DOC strain (control), GUS activity was detected in the presence of sorbose or sophorose. The Δcis strain showed very low GUS activity compared to the DOC strain even in the presence of any of sorbose and sophorose. In the 1Box strain and the 1RBox strain (the strain with the introduced modified promoter inserted with one Xyn1 promoter cis-element a complementary strand thereof), GUS activity in the presence of sophorose was increased 2.3-fold and 2.6-fold, respectively, compared to the DOC strain. In the 2Box strain (the strain with the introduced modified promoter inserted with two Xyn1 promoter cis-elements), GUS activity was increased 3.2-fold in the presence of sophorose. On the other hand, GUS activity in the presence of sophorose in the 2RBox strain (strain with introduced modified promoter inserted with two complementary strands of the Xyn1 promoter cis-element) was equivalent to that of the 1Box strain.

FIG. 2B shows GUS activity in liquid extracts of cells cultured in the presence of xylan substrates (xylose or xylan). No GUS activity could be detected in the DOC and 1Box strains when induction was carried out with xylan substrates. On the other hand, the 1RBox, 2Box and 2RBox strains showed GUS activity even in the presence of any of xylose and xylan.

The results in FIG. 2 show that the modified Xyn3 promoter to which the Xyn1 promoter cis-element was introduced can improve the inducibility by cellulosic substrate and can also acquire the inducibility by xylan substrate.

Example 4 Evaluation of Inducibility of Promoter (1) Preparation of Modified Xyn3 Promoters 3Box, 3RBox and 6RBox In accordance with the procedures of Example 1 (3), DNA fragments (3Box and 3RBox; SEQ ID NOs: 41 and 42) containing three cis-elements of the promoter of the gene encoding Xyn1 (SEQ ID NO:5) or complementary strands thereof, and containing XbaI sites at both ends were constructed. In addition, a DNA fragment (6RBox; SEQ ID NO:43) containing six complementary strands of the sequence represented by SEQ ID NO:5 and containing XbaI sites at both ends were synthesized. Each of these DNA fragments was used to prepare modified Xyn3 promoter-containing plasmids in the procedures of Example 1(4).

(2) Evaluation of Inducibility of Promoters

Figure 3:
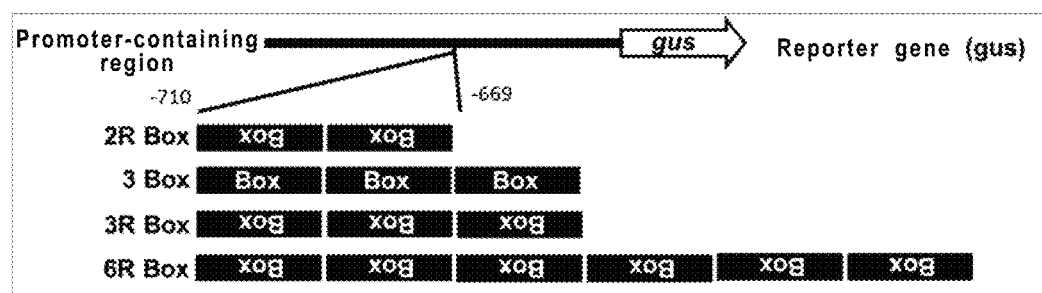
FIG. 3 shows the GUS reporter cassette in the transformant used in Example 4. Box: Xyn1 promoter cis-element.

In accordance with the procedures of Example 2, a GUS reporter cassette (FIG. 3) containing the modified Xyn3 promoter prepared in Example 1 was constructed, and then plasmid containing the GUS reporter cassette for promoter analysis were produced. Using the prepared plasmids, transformants 3Box strain, 3RBox strain, and 6RBox strain were prepared in accordance with the procedures of Example 3. The prepared transformants were used to determine GUS activity in liquid extracts of cells cultured in the presence of sophorose (FIG. 4A) or xylan (FIG. 4B). When the GUS activity of the wild-type (DOC strain) was defined as 100, the relative GUS activity was determined.

(3) Results

Figure 4:
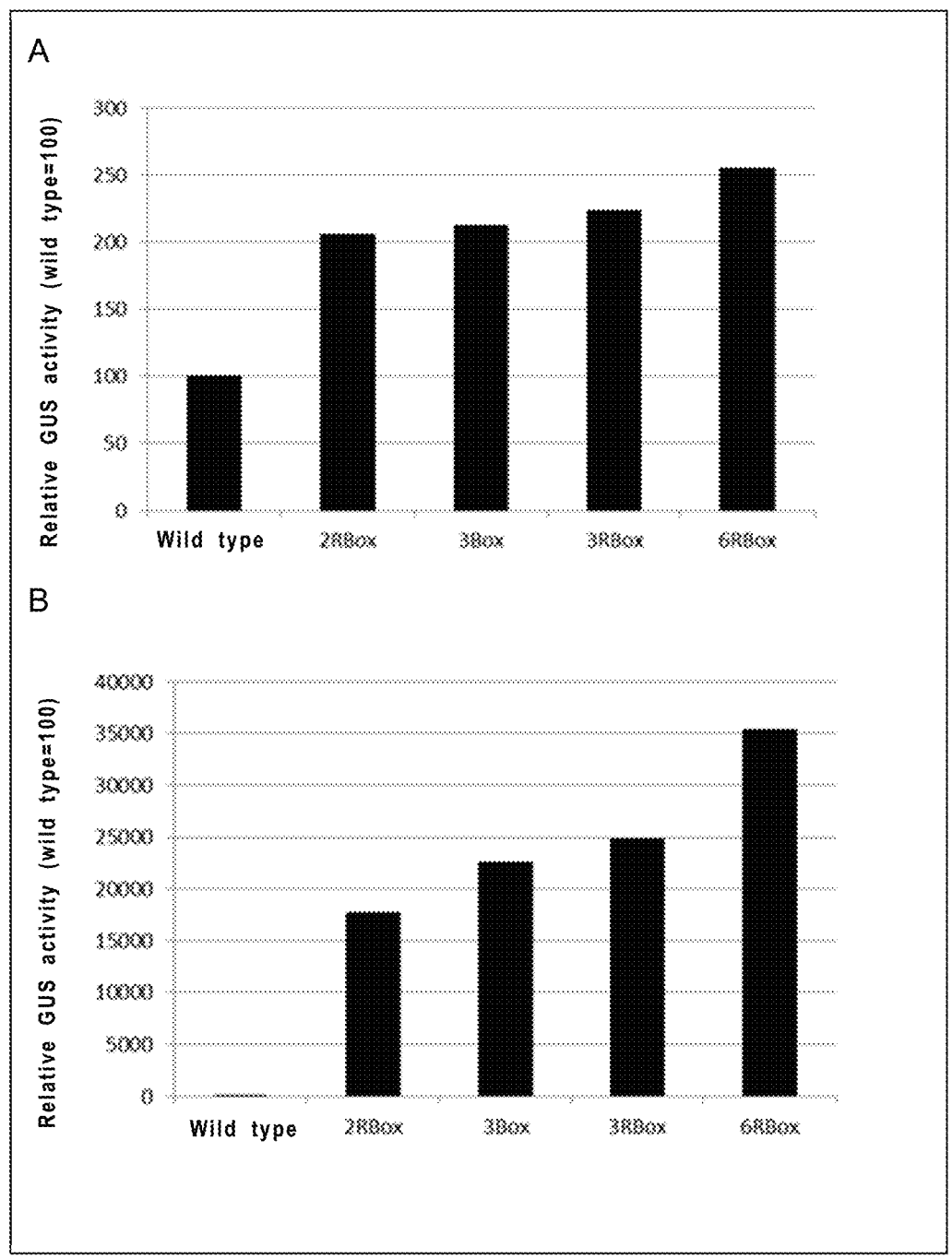
FIG. 4 shows the relative GUS activity in the liquid extract of modified promoter-introduced cells after induction culture. A: GUS Activity after culture in the presence of sophorose. B: GUS activity after culture in the presence of xylan.

FIG. 4 represents relative GUS activity for each transformant. FIG. 4 also shows data of 2RBox strain measured in Example 3. In the presence of any of sophorose and xylan, expression of GUS reporter was improved in the 3Box strain and 3RBox strain compared to the 2RBox strain, and further improved in the 6RBox strain. These results suggest that the promoter activity of the modified Xyn3 promoter is increased depending on the number of Xyn1 promoter cis-elements introduced.

Example 5 Evaluation of Enzyme Expression Using Modified Xyn3 Promoters (1) *Aspergillus aculeatus* Bgl1 (aabgl1) Expression cassette construction Using pABG7 (Biosci biotech biochem, 1998, 62(8): 1615-1618) as a template, PCR was performed using primer aabgl1_xyn3P (SEQ ID NO:19) added with an upstream sequence of xyn3 and primer aabgl1_xyn3T (SEQ ID NO:20) added with a downstream sequence of xyn3, to obtain a gene (aabgl1) fragment encoding β-glucosidase of a *Aspergillus aculeatus* (AaBGL1) to which the upstream and downstream sequences of xyn3 had been added at both ends. Inverse PCR was performed using pBxyn3ag-DOC as a template, primer aX3invert (SEQ ID NO:21) and primer aX3invert (SEQ ID NO:22). These PCR products were cloned using In-fusion PCR advanced kit (TaKaRaBio, Shiga, Japan) to obtain pBxyn3aabgl1. The pBxyn3aabgl carries the aabgl1 gene under the regulation of the upstream region of the xyn3 and the amdS gene as a selection marker at the Nan site of the downstream region. To recycle the marker, an inverse PCR product of pBxyn3aabgl1 (the amdS marker was removed) was constructed using pBxyn3aabgl1 as a template, primer recyinvert3a (SEQ ID NO:23) and primer recyinvert3a (SEQ ID NO:24).

Using the genomes of the PC-3-7 strain as a template, primer xyn3reps (SEQ ID NO:25) and primer xyn3repa (SEQ ID NO:26), a 748 bp of downstream region of the xyn3 was amplified and introduced into HincII site of the pUC118 (Takara) (pUxyn3DR). The pUxyn3DR was cleaved with EcoRV and BamHI to obtain a DNA fragment. Further, pBpyr4 (a plasmid obtained by cloning a DNA fragment containing pyr4 gene derived from of *Trichoderma reesei* and upstream and downstream regions thereof in pBluescriptII SK(+) (Novagen)) was cleaved with EcoRV and BamHI to obtain a DNA fragment. The obtained DNA fragment was subjected to ligation to obtain pBpyr4RM (a fragment obtained by inserting a downstream region of xyn3 downstream of pyr4 selection marker). Using the pBpyr4RM as a template, primer recyclex3s (SEQ ID NO:27) and primer recyclex3a (SEQ ID NO:28) to each of which the sequences of downstream region of xyn3 was added, respectively, the fragment was amplified. By subjecting the obtained amplified fragment and pBxyn3aabgl1 to In-Fusion, pBxyn3aabgl1pyr4RM was obtained The pBxyn3aabgl1pyr4RM was amplified by inverse PCR using primer xyn1-2Box_inv_Rv (SEQ ID NO:29) and primer Aabgl1_Fw (SEQ ID NO:30). Further, the pKFxyn3-2RBox was amplified using primer xyn1-2box_Fw (SEQ ID NO:31) and primer xyn1-2box_Rv (SEQ ID NO:32) to obtain a DNA fragment containing 2RBox region (SEQ ID NO:8). By subjecting these PCR products to ligation, pBxyn3_2RBaabgl1pyr4RM in which the upstream region of xyn3 was replaced by the promoter containing the 2RBox region was obtained.

(2) Acquisition of Transformant

The vector pBxyn3_2RBaabgl1pyr4RM constructed in (1) above was cleaved by SspI and NotI, and the resultant was introduced into a host to achieve transformation. Introduction was carried out by the protoplast PEG method (Biotechnol Bioeng, 2012, January; 109(1):92-99). The PC-3-7 strain was used as a host. Transformants were cultured in minimal medium without uridine for selection on the basis of uridine auxotrophy. Transformant candidate strains were cultured twice in minimal medium supplemented with acetamide or deprived of uridine and stabilized. Homologous recombination and introduced copies were confirmed by southern analysis using AlkPhos Direct kit (GE Healthcare Bio Science, Waukesha, Wis.). The resulting transformant was designated X3_2RB_AB1.

(3) Culture

Host and transformant were grown in Difco™ Potato Dextrose Agar (PDA) medium, and conidia were stored at −80° C. in a solution containing 0.9% (w/v) NaCl, and 10% (w/v) glycerol. For cellulase production, $1 \times 10^7$ conidia were inoculated in 50 ml of a medium with 1% (w/v) Avicel® (microcrystalline cellulose) or 1% (w/v) Avicel® and 0.5% (w/v) xylan as a carbon source (0.14% (w/v) $(NH_4)_2SO_4$, 0.2% (w/v) $KH_2PO_4$, 0.03% (w/v) $CaCl_2.2H_2O$, 0.03% (w/v) $MgSO_4.7H_2O$, 0.1% (w/v) Bacto™ Polypeptone, 0.05% (w/v) Bacto™ Yeast extract, 0.1% (w/v) Tween80, 0.1% (w/v) Trace element (supra), 50 mM tartrate Buffer (pH 4.0)), and cultured at 28° C., 220 rpm for 5 days. The culture supernatant was collected by filtration through Miracloth and used as an enzyme preparation.

(4) Enzyme Analysis

The enzymatic activity and protein amount were measured for the culture supernatants of X3_2RB_AB1 strain (BGL-activity enhanced strain by introduction of modified promoter) and PC-3-7 strain (host). The culture supernatants were subjected to SDS-PAGE with 12.5% polyacrylamide and stained with Coomassie Brilliant Blue R250. Precision Plus Dual Color Standard Marker (Bio-Rad Laboratories) was used for molecular weight determination. The protein amount was determined by the Bradford method using bovine immunoglobulin as a standard.

The avicelase, carboxymethyl cellulase (CMCase), and xylanase activities were calculated by measuring the amount of reducing sugars obtained by enzymatic reactions through the 3,5-dinitrosalicylic acid (DNS) method. The enzymatic reaction for measuring avicelase activity was carried out at 50° C. for 30 minutes using a reaction solution in which a final concentration of 1% (w/v) Avicel® was suspended in 50 mM sodium acetate buffer (pH 5.0). The enzymatic reaction for measuring the CMCase activity was carried out at 50° C. for 15 minutes using a reaction solution in which 40 mM carboxymethylcellulose (CMC) was dissolved in 50 mM sodium acetate buffer. The enzymatic reaction for measuring xylanase activity was carried out at 50° C. for 10 minutes using a reaction solution in which 1% (w/v) birch wood xylan was dissolved in 50 mM sodium acetate buffer. The activity of 1 U was defined as the amount of enzyme that produced 1 μmol equivalent of glucose (or xylose) in 1 minute. In measuring cellobiase activity, the enzyme was reacted at 50° C. for 10 minutes in a reaction solution in which a final concentration of 20 mM cellobiose (Sigma) was added to 50 mM acetate buffer, and then the glucose concentration was measured by Glucose C2 kit (Wako). The 1 U of cellobiase activity was defined as the amount of enzyme that produced 2 μmol of glucose in 1 minute.

Figure 5:
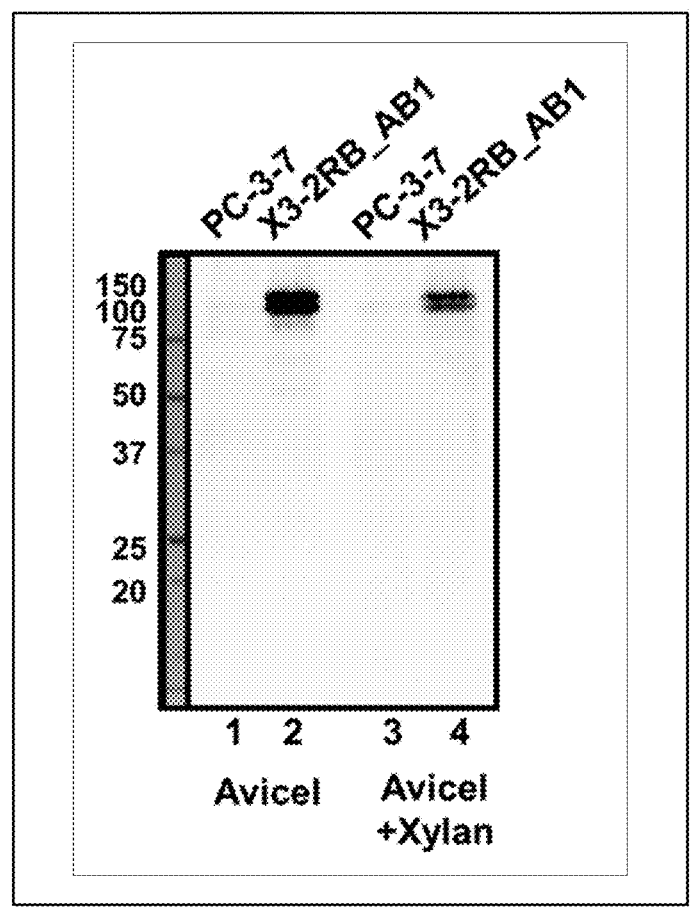
FIG. 5 shows a western blotting analysis of culture supernatant of PC-3-7 strain and X3-2RB_AB1 strain. Left: culture supernatant from a 1% Avicel® containing medium, right: culture supernatant from a 1% Avicel® and 0.5% xylan containing medium.

Expression of aaBGL in culture supernatant samples was observed using western blotting with an anti-BGL antibody. Western blotting was performed using a semi-dry blotting device (ATTO). After protein separation by SDS-PAGE, the protein was transcribed into Immobilon-P membrane (Merck Millipore). ECL select western blotting detection reagent (GE-Healthcare) was used to detect proteins. An antibody prepared by immunizing rabbits using purified aaBGL as an antigen was used as the anti aaBGL antibody. An HRP-labeled secondary antibody available from GE Healthcare was used to carry out detection. As a result of western blotting analysis, AaBGL1 bands were observed around 130 kDa in the X3_2RB_AB1 strain and not in the PC-3-7 strain (host) (FIG. 5). Two bands were observed around 130 kDa in the X3_2RB_AB1 strain, but any of these were not observed in the PC-3-7 strain (host), hence, it was considered that these were not a nonspecific band, and caused by a change in molecular weight size during the electrophoresis due to sugar chain modification to AaBGL.

Figure 7:
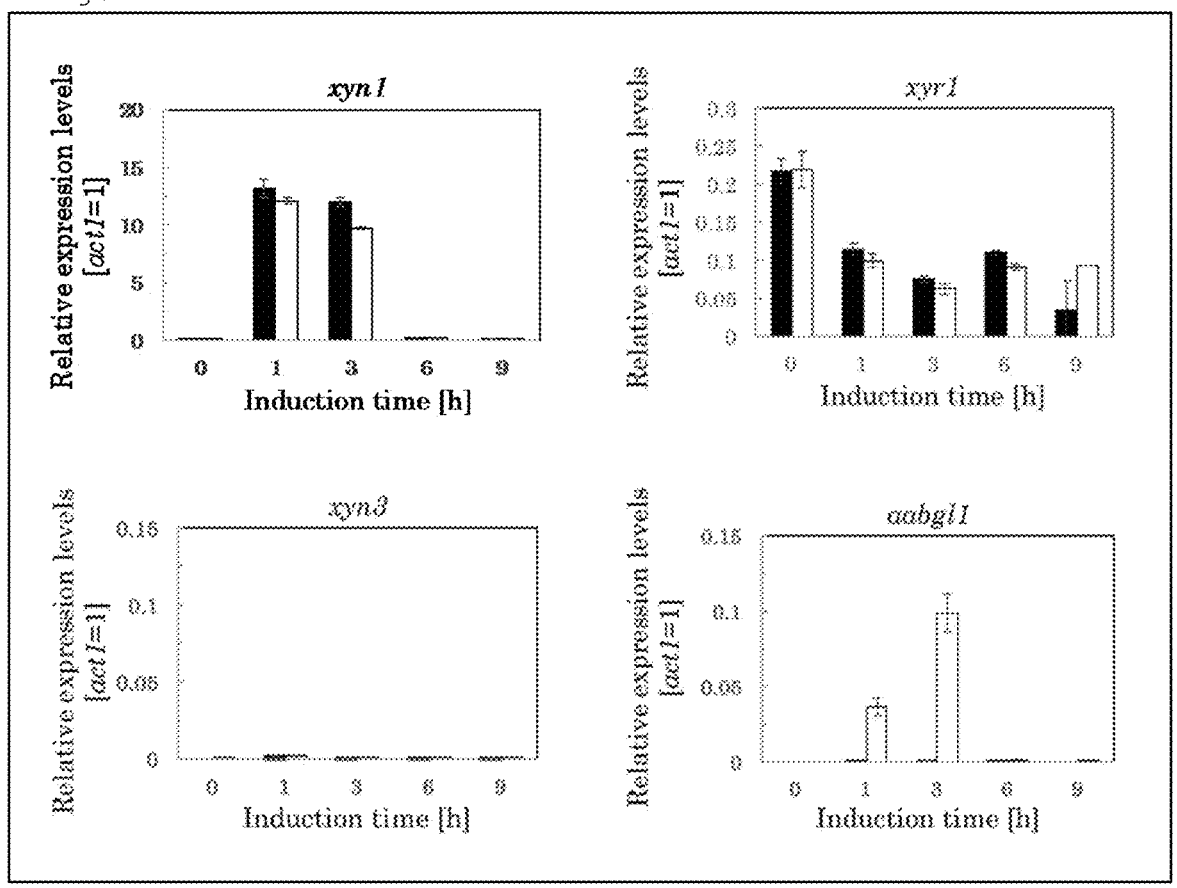
FIG. 7 shows the expression of xyn1, xyr1, xyn3 and aabgl1 genes in X3-2RB_AB1 strain and PC-3-7 strain under 0.1% xylan induction. White bar: X3-2RB_AB1 strain, black bar: PC-3-7 strain.

The measurement results of the protein amounts, and avicelase, CMCase, cellobiase, and xylanase activities in the X3_2RB_AB1 strain and PC-3-7 strain are shown in Table 1. The CMCase and xylanase activities were equivalent between the X3-2RB_AB1 strain and the PC-3-7 strain, but the cellobiase activity was 35.0 U/mL (Avicel® containing medium) and 17.7 U/mL (Avicel®+xylan containing medium) in the X3-2RB_AB1 strain, which were increased by about 120 and about 85 times, respectively, as compared to the PC-3-7 strain. The avicelase activity was also increased by about 30% in the X3-2RB_AB1 strain as compared to the host strain. These results suggest that the 2RBox promoter efficiently expressed the AaBGL1 gene ligated downstream in the culture in the presence of cellulose or cellulose and xylans.

a higher level (FIG. 7). These results are consistent with previous findings on the promoter activity of these genes. On the other hand, in X3-2RB_AB1 strain, expression of aabgl1 was observed both under sophorose-induction and xylan-induction, indicating that these inducers activated the modified Xyn3 promoter.

Example 6 Expression of AaBGL1 by Modified Xyn3 Promoter in QM9414 Strain (Xyn3 Nonexpressing Strain)

Xyn3 is originally expressed in the *Trichoderma reesei* PC-3-7 strain, but not in its ancestor, the *Trichoderma reesei* QM9414 strain. In this example, the possibility that the modified Xyn3 promoter can show its function in the QM9414 strain was considered.

In the same manner as in Example 5 except that the QM9414 strain was used as a host of the transformant, a transformant QMX3-2 RB-AB1 was prepared, the transformant QMX3-2 RB-AB1 into which a plasmid pBxyn3-2RBaabgl1pyr4RM had been introduced, the plasmid

TABLE 1

| | Culture condition | Protein concentration mg/ml | Avicelase activity [U/ml] | CMCase activity [U/ml] | cellobiase activity [U/ml] | xylanase activity [U/ml] |
|---|---|---|---|---|---|---|
| PC-3-7 | Avicel | 1.44 ± 0.01 | 0.685 ± 0.023 | 33.7 ± 0.9 | 0.289 ± 0.030 | 179 ± 7 |
| | Avicel + xylan | 1.42 ± 0.03 | 0.695 ± 0.054 | 30.6 ± 1.0 | 0.207 ± 0.019 | 265 ± 2 |
| X3-2RB_AB1 | Avicel | 1.44 ± 0.01 | 0.911 ± 0.004 | 38.3 ± 0.7 | 35.0 ± 3.9 | 180 ± 7 |
| | Avicel + xylan | 1.41 ± 0.01 | 0.915 ± 0.007 | 33.7 ± 1.6 | 17.7 ± 3.4 | 270 ± 9 |

(5) Transcriptional Analysis

To evaluate the transcriptional level of the modified Xyn3 promoter, transcriptional analyses of the PC-3-7 strain and X3-2RB_AB1 strain were performed. The PC-3-7 strain and X3-2RB_AB1 strain were cultured in 0.3% (w/v) glucose-containing medium for 2 days to obtain resting cells. The resulting cells were incubated for 1, 3, 6, and 9 hours in induction medium with 0.01% (w/v) sophorose (cellulose-based substrate, strong cellulase inducer) or 0.1% (w/v) xylan (xylan-based substrate) as a single carbon source, followed by transcriptional analysis to determine gene expression. As target genes of transcription analysis, main cellulase gene cbh1, main xylanase gene xyn1, transcriptional activator xyr1 essential for cellulase production, xylanase gene xyn3, and aabgl1 were analyzed. Gene expression was measured by quantitative real-time PCR, and the relative expression level was determined when the expression level of β-actin (act1) was 1.

Figure 6:
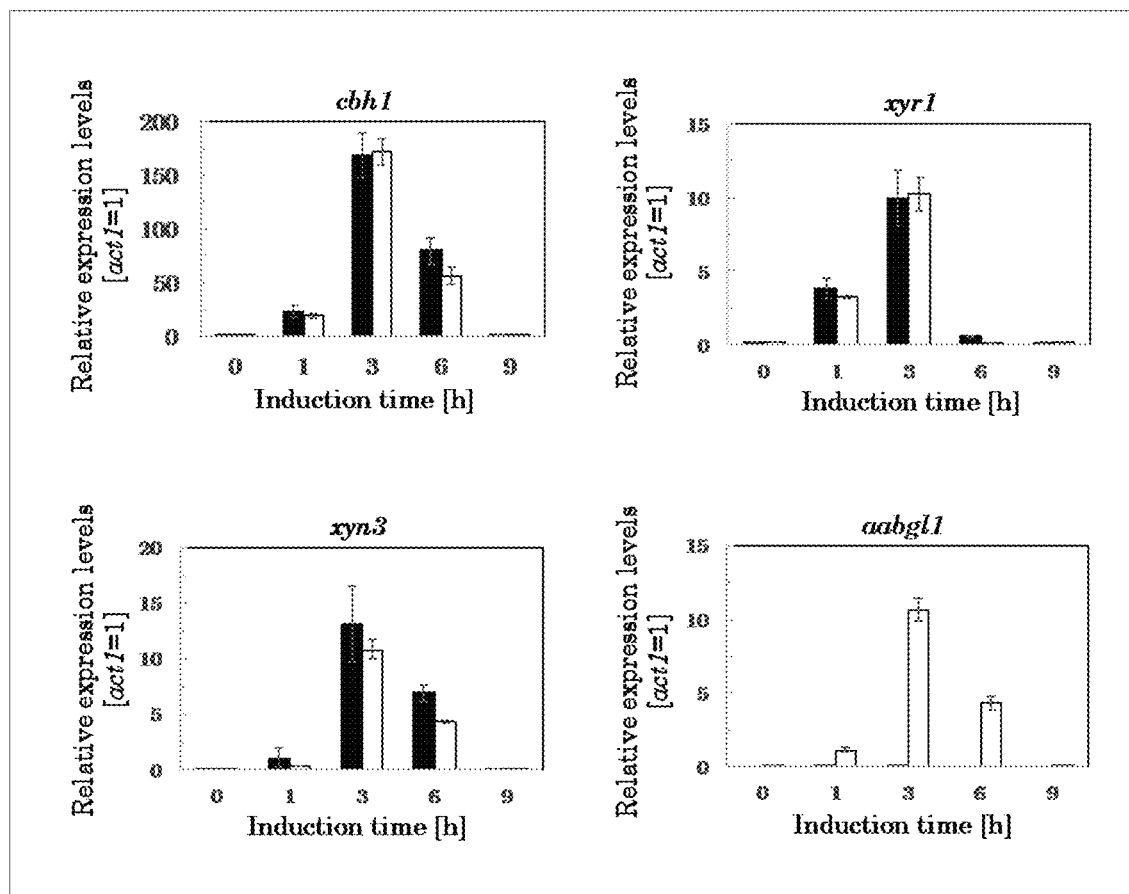
FIG. 6 shows the expression of cbh1, xyr1, xyn3 and aabgl1 genes in X3-2RB_AB1 strain and PC-3-7 strain under 0.01% sophorose induction. White bar: X3-2RB_AB1 strain, black bar: PC-3-7 strain.

The results are shown in FIG. 6 and FIG. 7. Under sophorose-induction, cbh1, xyr1, and xyn3 expression levels were similar between the PC-3-7 strain and the X3-2RB_AB1 strain (FIG. 6). Also, as is conventionally known in the art, xyn1 was not expressed under sophorose-induction (data not shown). On the other hand, under xylan-induction, neither the PC-3-7 strain nor the X3-2RB_AB1 strain expressed xyn3, but expressed xyn1 at pBxyn3-2RBaabgl1pyr4RM containing an expression cassette into which aabgl1 was introduced under regulation of the modified Xyn3 promoter containing a 2RBox region (SEQ ID NO:8). In addition, the enzymatic activities in the QMX3-2 RB_AB1 strain and the host QM9414 strain were measured in the same manner as in Example 5 (4). However, the concentration of xylan in the induction medium was 0.01% (w/v). Further, the transcriptional activity of aabgl1 was examined in the same manner as in Example 5 (5).

Figure 8:
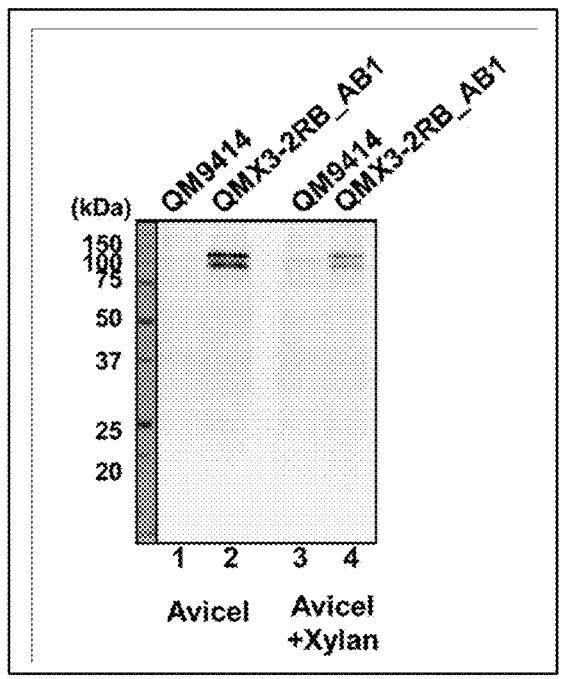
FIG. 8 shows a western blotting analysis of culture supernatant of QM9414 strain and QMX3-2RB_AB1 strain. Left: culture supernatant from a 1% Avicel® containing medium, right: culture supernatant from a 1% Avicel® and 0.5% xylan containing medium.
Figure 9:
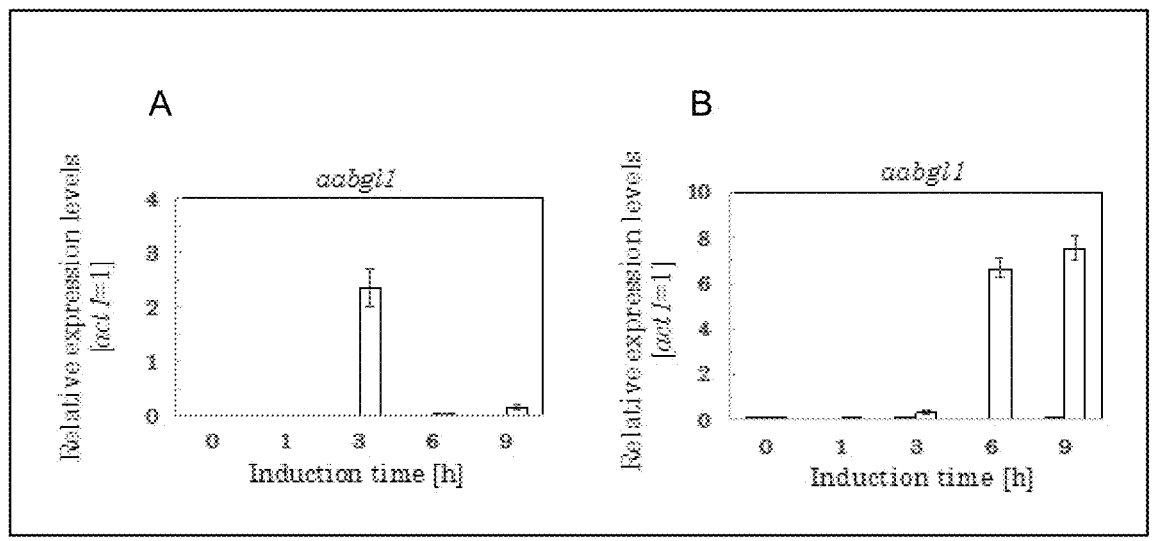
FIG. 9 shows the expression of aabgl1 gene in QMX3-2RB_AB1 strain and QM9414 strain. A: under 0.01% sophorose induction, B: under 0.01% xylan induction. White bar: QMX3-2 RB_AB1 strain, black bar: QM9414 strain.

In western blotting analysis of the culture supernatant of QMX3-2RB_AB1 strain, AaBGL1 bands were observed (FIG. 8). In addition, the QMX3-2RB_AB1 strain exhibited the protein amount, avicelase activity and cellobiase activity at an increased value, as compared to the QM9414 strain (host) (Table 2). As a result of transcriptional analysis, it was confirmed that in the QMX3-2RB_AB1 strain, transcription of aabgl1 was confirmed both under sophorose (cellulosic substrate)-induction (FIG. 9A) and under xylan (xylan-based substrate)-induction (FIG. 9B), indicating that transcription of aabgl1 was promoted under regulation of the modified promoter.

TABLE 2

|  | Culture condition | Protein concentration mg/ml | Avicelase activity [U/ml] | CMCase activity [U/ml] | cellobiase activity [U/ml] | xylanase activity [U/ml] |
|---|---|---|---|---|---|---|
| QM9414 | Avicel | 0.93 ± 0.01 | 0.629 ± 0.013 | 30.1 ± 0.8 | 0.390 ± 0.041 | 55.7 ± 1.9 |
|  | Avicel + xylan | 0.85 ± 0.03 | 0.639 ± 0.005 | 28.3 ± 0.8 | 0.251 ± 0.008 | 95.7 ± 2.1 |
| QMX3-2RB_AB1 | Avicel | 0.97 ± 0.01 | 0.859 ± 0.047 | 35.3 ± 0.5 | 13.9 ± 2.4 | 59.9 ± 0.2 |
|  | Avicel + xylan | 0.88 ± 0.02 | 0.781 ± 0.032 | 29.5 ± 1.9 | 12.5 ± 0.7 | 90.4 ± 6.7 |

Example 7 Evaluation of Xyn3 Expression Using Modified Xyn3 Promoter (1) Construction of *Trichoderma reesei* Xyn3 Expression Cassette A DNA fragment containing a 2,274 bp of upstream region and a 1,244 bp of downstream region of pyr4 and pyr4 ORF were obtained using the PC-3-7 strain genome as a template, and primer pyr4_Fw (SEQ ID NO:33) and primer pyr4_Rv (SEQ ID NO:34). This DNA fragment was inserted into a pUC118 linearized with HincII, and pUΔpyr4 was produced.

The pBxyn3-2RBaabgl1pyr4RM produced in Example 5 was used as a template, and inverse PCR was performed using primer aX3invert (SEQ ID NO:21) and primer sX3invert (SEQ ID NO:22). In addition, xyn3 ORF was amplified using the PC-3-7 strain genomic DNA as a template and primer xyn3_Fw (SEQ ID NO:35) and primer xyn3_Rv (SEQ ID NO:36), and phosphate group-addition was performed with Blunting Kination kit (TaKaRa). These DNA fragments were ligated to produce pBxyn3_2RBxyn3pyr4RM.

(2) Acquisition of Transformant

The pUΔpyr4 produced in (1) was digested with HindIII and XbaI to prepare a fragment, which was introduced into a host by the protoplast-PEG method. The E1AB1 strain (Enzyme Microb Technol, 2016, 82:89-95) was used as a host strain. Selection was performed on a minimal medium supplemented with 10 mM FOA and 20 mM uridine to obtain the E1AB1Δpyr4 strain. Next, a fragment obtained by digesting pBxyn3_2RBxyn3pyr4RM produced in (1) with ApaI and NotI was introduced into the E1AB1Δpyr4 strain. Among the transformant candidates selected in the minimal medium without uridine, the transformant exhibiting the highest saccharifying ability was obtained as the E1AB1_X3-2RBX3 strain.

(3) Culture of Transformant

The enzyme productivity of the transformant was evaluated by the following culture. As a preculture, 50 mL of culture medium was charged to a 500 mL flask, and spores were inoculated at 1×10⁵ spores/mL, followed by shaking and culturing at 28° C. and 220 rpm (PRXYg-98R manufactured by Preci Co., Ltd.). The medium composition is as follows: 1% (w/v) glucose, 0.14% (w/v) $(NH_4)_2SO_4$, 0.2% (w/v) $KH_2PO_4$, 0.03% (w/v) $CaCl_2.2H_2O$, 0.03% (w/v) $MgSO_4.7H_2O$, 0.1% (w/v) high polypeptone N, 0.05% (w/v) Bacto Yeast extract, 0.1% (w/v) Tween 80, 0.1% (w/v) Trace element 2, and 50 mM tartaric acid buffer (pH 4.0). The composition of the Trace element 2 was as follows: 6 mg $H_3BO_3$, 26 mg $(NH_4)_6Mo_7O_{24}.4H_2O$, 100 mg $FeCl_3.6H_2O$, 40 mg $CuSO_4.5H_2O$, 8 mg $MnCl_2.4H_2O$, and 200 mg $ZnCl_2$ were scaled up to 100 ml with distilled water.

After 2 days of preculture, the main culture was performed using a jar fermenter (BTR-25NA1S-8M manufactured by Biot inc.). The precultured fluid was inoculated in an amount of 10% (v/v) and cultured for 5 days. 10% (w/v) Avicel®+2% (w/v) xylan was served as a carbon source, with the remaining medium components being 0.42% (w/v) $(NH_4)_2SO_4$, 0.2% (w/v) $KH_2PO_4$, 0.03% (w/v) $CaCl_2.2H_2O$, 0.03% (w/v) $MgSO_4.7H_2O$, 0.1% (w/v) high polypeptone N, 0.05% (w/v) Bacto Yeast extract, 0.1% (w/v) Tween80, 0.1% (w/v) Trace element (supra), and 0.2% (w/v) Antifoam PE-L. The setting of the jar fermenter is as follows: temperature 28° C., pH 4.5, stirring speed varied to keep DO=3.0 ppm constantly.

The culture supernatant was collected in the same manner as in Example 5 (3), and the concentration of protein was measured by the bradford method. In the bradford method, a Quick Start protein assay (BioRad) was used, and the protein amount was calculated based on a standard curve using bovine gamma globulin as a standard protein. At the time, the relative ratio of the protein amount in the culture supernatant (JN24) of the E1AB1_X3-2RBX3 strain when the protein amount in the culture supernatant (JN13) of the E1AB1 strain was set to 1. As a result, the protein productivity of JN24 was improved by 23% compared with that of the JN13 strain.

Figure 10:
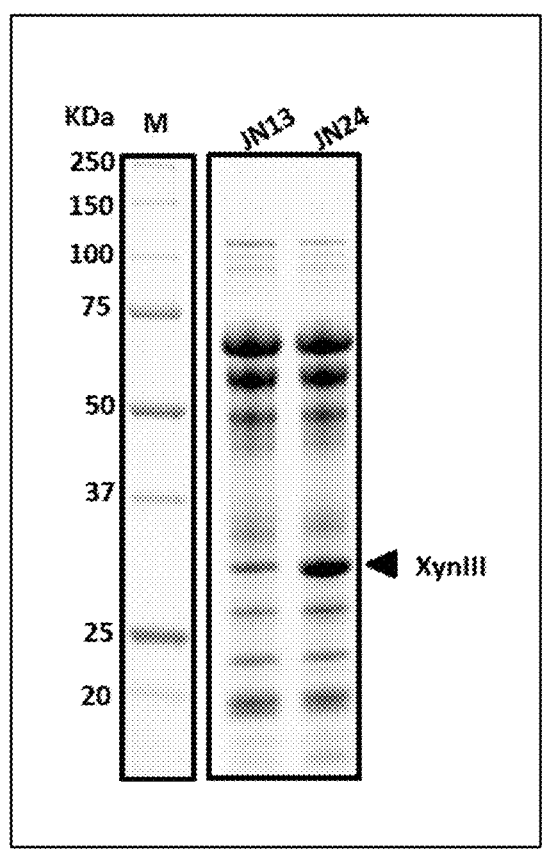
FIG. 10 shows a SDS-PAGE analysis of culture supernatant of E1AB1 strain (JN13) and E1AB1_X3-2RBX3 strain (JN24).

As a result of SDS-PAGE analysis of the respective culture supernatants, it was observed that only Xyn3 band was greatly increased in JN24 compared with the JN13 which was the culture supernatant of the original strain (FIG. 10). The shades of the SDS-PAGE bands were quantified using Image Lab (Bio-rad Laboratories) to calculate the protein amount ratios of each enzyme. As a result of calculating and comparing the calculated values and the amounts of enzymes contained in JN13 and JN24, respectively, from the protein amounts in the supernatant, the amounts of most enzymes were equivalent between JN13 and JN24, whereas only Xyn3 was increased by more than 4-fold in JN24. Accordingly, it was found that most of the proteins showing an improved production in JN24 were Xyn3. This indicates that the modified Xyn3 promoter is a promoter capable of expressing proteins highly even in a jar fermenter culture.

The sequences of the primers used in the above examples are shown in Tables 3 to 4 below.

TABLE 3

| Name | sequence (5'→3') | SEQ ID NO: |
|---|---|---|
| xyn3-EcoRI-U | GGGAATTCCGTGATTGACAAAATCTATTCG | 9 |
| xyn3-NcoI | GGTGCTTCCATGGTGTCCGCCTCAATTG | 10 |
| xyn3P_cis_inv_Fw | AGAATTTCAGTCCGGGTATTTAGACT | 11 |

TABLE 3-continued

| Name | sequence (5'→3') | SEQ ID NO: |
|---|---|---|
| xyn3P_cis_inv_Rv | AGACAGTTTCGGTCAAGGCATTG | 12 |
| 1Box_Fw | CTGTCTAGAGGCTAAGATGTCGCATTTAGCCTCTAGAATT | 13 |
| 1Box_Rv | AATTCTAGAGGCTAAATGCGACATCTTAGCCTCTAGACAG | 14 |
| xyn3-SpeI | CCACTAGTCTGCTACATGGGTATGGCAG | 15 |
| xyn3-EcoRI-D | CCGAATTCAAGGCGTCCCTCGG | 16 |
| gus-NcoI | CCCACCTATAACCATGGTCCGTCCTGTAG | 17 |
| gus-SpeI | CCACTAGTTATTGTTTGCCTCCCTGCTGCG | 18 |
| aabgl1_xyn3P | TGAGTTTCAATTGAGGCGGACAATATGAAGCTCAGTTGGCTTGAG | 19 |
| aabgl1_xyn3T | CTGCCATACCCATGTAGCAGAGCATTCATTGCACCTTCGGGAGCG | 20 |
| aX3invert | ATTGTCCGCCTCAATTGAAACTCAGTGGAAAGATGGTAG | 21 |
| sX3invert | ATGCTCTGCTACATGGGTATGGCAGGGTCGG | 22 |

TABLE 4

| Name | sequence (5'→3') | SEQ ID NO: |
|---|---|---|
| recyinvert3a | CCGCCTTGTTTCAGGGTCGAGGC | 23 |
| recyinvert3s | GCCTCGACCCTGAAACAAGGCGG | 24 |
| xyn3reps | ATCTCAAGAGTCTAGTATATGACGGTATCTCTAGA | 25 |
| xyn3repa | GCCTCGACCCTGAAACAAGGC | 26 |
| recyclex3s | GCCGCCTTGTTTCAGGGTCGAGGCCCAGGGGACGAGCCCGACATTAAAG | 27 |
| recyclex3a | AATTCAAGGCGTCCCTCGGCGGCGCCTCGACCCTGAAACAAGGCGGCGAC | 28 |
| xyn1_2Box_inv_Rv | TCTCTATTTCGCAGGCGATAAC | 29 |
| Aabgl1_Fw | ATGAAGCTCAGTTGGCTTGAG | 30 |
| xyn1_2box_Fw | GAATTCCGTGATTGACAAAATC | 31 |
| xyn1_2box_Rv | ATATTGTCCGCCTCAATTG | 32 |
| pyr4_Fw | CGAGTTGTCTAGACTCGACTCGACTTGCG | 33 |
| pyr4_Rv | GCGGAGGCGAGGGCTGTTGTGCGAAT | 34 |
| xyn3_Fw | ATGAAAGCAAACGTCATCTTGTGCCTCCT | 35 |
| xyn3_Rv | CTATTGTAAGATGCCAACAATGCTGTTATATGCCGG | 36 |

What is claimed is:

1. A modified promoter comprising:
   (a) a polynucleotide comprising the sequence of an Xyn3 promoter, wherein the polynucleotide that comprises the sequence of the Xyn3 promoter also comprises
   (b) a polynucleotide comprising the sequence of at least one Xyn1 promoter cis-element or a complementary strand thereof,
   wherein the sequence of the cis-element polynucleotide is present in a region corresponding to position 374 to 401 of SEQ ID NO:1 such that the sequence in the region corresponding to SEQ ID NO:1 position 374-401 is partially or completely deleted, or interrupted by the polynucleotide that comprises the Xyn1 cis-element,
   wherein the sequence of the Xyn3 polynucleotide is:
   a polynucleotide consisting of the nucleotide sequence of SEQ ID NO:1;
   or
   a polynucleotide consisting of the nucleotide sequence of the nucleotides at position 350 to 1084 of SEQ ID NO:1; or
   a polynucleotide consisting of a nucleotide sequence that has an identity of at least 90% with the nucleotide sequence of SEQ ID NO:1, or with the nucleotide sequence of the nucleotides at position 350 to 1084 of SEQ ID NO:1, and that comprises the sequence GGC-TAT-NNNNNNNNNNNNNNNNN-TTTGCC (SEQ ID NO:2) in a region corresponding to the nucleotides at position 374 to 401 of SEQ ID NO:1, and that has promoter activity induced by cellulose,
   wherein the sequence of the polynucleotide of the Xyn1 promoter cis-element consists of the nucleotide sequence GGCTAA-NNNNNNNNNN-TTAGCC (SEQ ID NO:4); and wherein the sequence of the polynucleotide that comprises at least one Xyn1 promoter cis-element or a complementary strand thereof does not comprise a HAP2/3/5 binding site or a CREI binding site.

2. The modified promoter according to claim 1, wherein the sequence of the Xyn3 polynucleotide is:
a polynucleotide consisting of the nucleotide sequence of SEQ ID NO:1; or
a polynucleotide consisting of the nucleotide sequence of the nucleotides at position 350 to 1084 of SEQ ID NO:1; or
a polynucleotide consisting of a nucleotide sequence that has an identity of at least 95% with the nucleotide sequence of SEQ ID NO:1 or with the nucleotide sequence of the nucleotides at position 350 to 1084 of SEQ ID NO:1, and comprises the sequence of SEQ ID NO:2 in a region corresponding to the nucleotides at position 374 to 401 of SEQ ID NO:1, and that has promoter activity induced by cellulose.

3. The modified promoter according to claim 1, wherein the sequence of the Xyn3 polynucleotide is:
a polynucleotide consisting of the nucleotide sequence of the nucleotides at position 3 to 1073 of SEQ ID NO:1;
a polynucleotide consisting of the nucleotide sequence of the nucleotides at position 350 to 1073 of SEQ ID NO:1; or
a polynucleotide consisting of a nucleotide sequence that has an identity of at least 90% of the nucleotide sequence of the nucleotides at position 3 to 1073 of SEQ ID NO:1; or the nucleotide sequence of the nucleotides at position 350 to 1073 of SEQ ID NO:1, and comprises the sequence of SEQ ID NO:2 in a region corresponding to the nucleotides at position 374 to 401 of SEQ ID NO:1, and that has promoter activity induced by cellulose.

4. The modified promoter according to claim 1, which comprises up to 10 cis-elements consisting of SEQ ID NO:4 or a complementary strand thereof.

5. The modified promoter according to claim 4, which comprises up to 10 cis-elements consisting of SEQ ID NO:5 or a complementary strand thereof.

6. The modified promoter according to claim 4, wherein the polynucleotide that comprises at least one Xyn1 promoter cis-element or a complementary strand thereof is the following:
a polynucleotide consisting of the nucleotide sequence of SEQ ID NO:6 or a complementary strand thereof;
a polynucleotide consisting of the nucleotide sequence of SEQ ID NO:7;
a polynucleotide consisting of the nucleotide sequence of SEQ ID NO:8;
a polynucleotide consisting of the nucleotide sequence of SEQ ID No:41;
a polynucleotide consisting of the nucleotide-sequence of SEQ ID No:42; or
a polynucleotide consisting of the nucleotide sequence of SEQ ID No:43.

7. A vector comprising the modified promoter according to claim 1.

8. The vector according to claim 7, wherein the modified promoter is ligated upstream of a gene of interest.

9. The vector according to claim 8, wherein the gene of interest is a polynucleotide encoding xylanase consisting of the nucleotide sequence of SEQ ID NO:37 or consisting of a nucleotide sequence having an identity of at least 90% therewith or a polynucleotide encoding xylanase consisting of the nucleotide sequence of SEQ ID NO:39 or consisting of a nucleotide sequence having an identity of at least 90% therewith.

10. A DNA fragment comprising a gene of interest and the modified promoter according to claim 1 operably ligated upstream of the gene.

11. The DNA fragment according to claim 10, wherein the gene of interest is a polynucleotide encoding xylanase consisting of the nucleotide sequence of SEQ ID NO:37 or consisting of a nucleotide sequence having an identity of at least 90% therewith or a polynucleotide encoding xylanase consisting of the nucleotide sequence of SEQ ID NO:39 or consisting of a nucleotide sequence having an identity of at least 90% therewith.

12. A transformant comprising the vector according to claim 7.

13. The transformant according to claim 12, which is a member of the genus *Trichoderma*.

14. A method for producing a modified promoter, comprising:
substituting or inserting a polynucleotide that comprises at least one Xyn1 promoter cis-element polynucleotide or a complementary strand thereof into a region corresponding to the nucleotides at position 374 to 401 of SEQ ID NO:1 in a Xyn3 promoter polynucleotide, such that the sequence in the region corresponding to SEQ ID NO:1 position 374-401 is partially or completely deleted, or interrupted by the polynucleotide that comprises the Xyn1 cis-element,
wherein the sequence of the Xyn3 promoter polynucleotide is:
a polynucleotide consisting of the nucleotide sequence of SEQ ID NO:1;
a polynucleotide consisting of the nucleotide sequence of the nucleotides at position 350 to 1084 of SEQ ID NO:1; or
a polynucleotide consisting of a nucleotide sequence that has an identity of at least 90% with the nucleotide sequence of SEQ ID NO:1, or with the sequence of the nucleotides at position 350 to 1084 of SEQ ID NO:1 and that comprises the sequence GGCTAT-NNNNNNNNNNNNNNNN-TTTGCC (SEQ ID NO:2) in a region corresponding to the nucleotides at position 374 to 401 of SEQ ID NO:1, and that has promoter activity induced by cellulose,
wherein the polynucleotide sequence of the Xyn1 promoter cis-element consists of the nucleotide sequence GGCTAA-NNNNNNNNNN-TTAGCC (SEQ ID NO:4) and
wherein the polynucleotide sequence that comprises at least one Xyn1 promoter cis-element or a complementary strand thereof does not comprise HAP2/3/5 binding site or a CREI binding site.

15. The method according to claim 14, wherein the sequence of the Xyn3 polynucleotide is:
a polynucleotide consisting of the nucleotide sequence of SEQ ID NO:1; or
a polynucleotide consisting of the nucleotide sequence of the nucleotides at position 350 to 1084 of SEQ ID NO: 1; or
a polynucleotide consisting of a nucleotide sequence that has an identity of at least 95% with the nucleotide sequence of SEQ ID NO:1, or with the sequence of the nucleotides at position 350 to 1084 of SEQ ID NO:1 and that comprises the sequence of SEQ ID NO:2 in a region corresponding to the nucleotides at position 374 to 401 of SEQ ID NO:1, and that has promoter activity induced by cellulose.

16. The method according to claim 14, wherein the sequence of the Xyn3 promoter polynucleotide is the following:
- a polynucleotide consisting of the nucleotide sequence of the nucleotides at position 3 to 1073 of SEQ ID NO:1; or
- a polynucleotide consisting of the nucleotide sequence of the nucleotides at position 350 to 1073 of SEQ ID NO:1; or
- a polynucleotide consisting of a nucleotide sequence that has an identity of at least 90% with the nucleotide sequence of the nucleotides at position 3 to 1073 of SEQ ID NO:1, or the nucleotide sequence of the nucleotides at position 350 to 1073 of SEQ ID NO:1 and that comprises the sequence of SEQ ID NO:2 in a region corresponding to the nucleotides at position 374 to 401 of SEQ ID NO:1, and having promoter activity induced by cellulose.

17. The method according to claim 14, wherein the modified promoter comprises up to 10 cis-elements consisting of SEQ ID NO:4 or a complementary strand thereof.

18. The method according to claim 17, wherein the modified promoter comprises up to 10 cis-elements consisting of SEQ ID NO:5 or a complementary strand thereof.

19. The method according to claim 17, wherein the polynucleotide that comprises at least one polynucleotide of the Xyn1 promoter cis-element or a complementary strand thereof is the following:
- a polynucleotide consisting of the nucleotide sequence of SEQ ID NO:6 or a complementary strand thereof;
- a polynucleotide consisting of the nucleotide sequence of SEQ ID NO:7;
- a polynucleotide consisting of the nucleotide sequence of SEQ ID NO:8;
- a polynucleotide consisting of the nucleotide sequence of SEQ ID NO:41;
- a polynucleotide consisting of the nucleotide sequence of SEQ ID NO:42; or
- a polynucleotide consisting of the nucleotide sequence of SEQ ID NO:43.

20. A transformant comprising the DNA fragment according to claim 10.

* * * * *